United States Patent
Sun et al.

(10) Patent No.: US 10,465,167 B2
(45) Date of Patent: Nov. 5, 2019

(54) ADJUVANT FOR RAPID PROLIFERATION OF HUMAN MESENCHYMAL STEM CELLS IN VITRO, METHOD FOR RAPID PROLIFERATION OF HUMAN MESENCHYMAL STEM CELLS IN VITRO, METHOD FOR GROWTH FACTOR HARVESTED FROM RAPID PROLIFERATION OF HUMAN MESENCHYMAL STEM CELLS IN VITRO AND USE THEREOF

(71) Applicant: BUDDHIST TZU CHI MEDICAL FOUNDATION, Hualien County (TW)

(72) Inventors: Li-Yi Sun, Hualien County (TW); Cheng-Yoong Pang, Hualien County (TW); Ching-Feng Cheng, Hualien County (TW); Dian-Kun Li, Hualien County (TW)

(73) Assignee: Hualien Tzu Chi Hospital, Buddhist Tzu Chi Medical Foundation, Hualien (TW)

( * ) Notice: Subject to any disclaimer, the term of this patent is extended or adjusted under 35 U.S.C. 154(b) by 0 days.

(21) Appl. No.: 14/102,593

(22) Filed: Dec. 11, 2013

(65) Prior Publication Data

US 2015/0159137 A1 Jun. 11, 2015

(51) Int. Cl.
C12N 5/0775 (2010.01)

(52) U.S. Cl.
CPC ........ C12N 5/0667 (2013.01); *C12N 2500/02* (2013.01); *C12N 2500/38* (2013.01); *C12N 2501/115* (2013.01)

(58) Field of Classification Search
CPC .............. C12N 5/0667; C12N 2500/02; C12N 2500/38; C12N 2501/115
See application file for complete search history.

(56) References Cited

U.S. PATENT DOCUMENTS 7,972,767 B2 * 7/2011 Lin .................................... 435/2
2009/0170200 A1 * 7/2009 Yeh et al. ..................... 435/384

OTHER PUBLICATIONS

Liu et al. "Cryopreservation of Human Bone Marrow-Derived Mesenchymal Stem Cells with Reduced Dimethylsulfoxide and Well-Defined Freezing Solutions." (Jun. 2010) Biotechnology Progress: vol. 26, No. 6: 1635-1643.*
Caplan et al. "Mesenchymal stem cells: building blocks for molecular medicine in the $21^{st}$ century" (Jun. 2001) Trends in Molecular Medicine, vol. 7, No. 6: 259-264.*
Haynesworth et al. "Cytokine Expression by Human Marrow-Derived Mesenchymal Progenitor Cells in Vitro: Effects of Dexamethasone and IL-1." (1996) Journal of Cellular Physiology, vol. 166: 585-592.*
Young et al. "Use of Mesenchymal Stem Cells in a Collagen Matrix for Achilles Tendon Repair" (1998) Journal of Orthopaedic Research, vol. 16, No. 4: 406-413.*
Mayer et al. "Vascular Endothelial Growth Factor (VEGF-A) Expression in Human Mesenchymal Stem Cells: Autocrine and Paracrine Role on Osteoblastic and Endothelial Differentiation" (2005) Journal of Cellular Biochemistry, vol. 95: 827-839.*
Shandadfar et al. "In Vitro Expansion of Human Mesenchymal Stem Cells: Choice of Serum is a Determinant of Cell Proliferation, Differentiation, Gene Expression and Transcriptome Stability." (2005) Stem Cells, vol. 23: 1357-1366.*
Deorosan et al. "The Role of Glucose, Serum, and Three-Dimensional Cell Culture on the Metabolism of Bone Marrow-Derived Mesenchymal Stem Cells" (2011), Stem Cells International, vol. 2011, article ID 429187, 1-12. (Year: 2011).*
Sun et al. "Antioxidants cause rapid expansion of human adipose-derived mesenchymal cells via CDK and CDK inhibitor regulation" (2013), vol. 20:53, pp. 1-11. (Year: 2013).*

* cited by examiner

*Primary Examiner* — Louise W Humphrey
*Assistant Examiner* — Teresa E Knight
(74) *Attorney, Agent, or Firm* — McCarter & English, LLP; Yu Lu

(57) ABSTRACT

An adjuvant for rapid proliferation of human mesenchymal stem cells in vitro is provided to overcome the problem of low cell amplification efficiency of human mesenchymal stem cells in a culture process. The adjuvant added for the culture of human mesenchymal stem cells includes at least one antioxidant, and a basic fibroblast growth factor (FGF-2). The adjuvant is added into a medium containing the human mesenchymal stem cells, and the culture takes place in a normal oxygen environment (21% oxygen tension), and the cells are divided rapidly, and the cell cycle at synthesis phase (S phase) percentage is increased to reduce ageing and improve differentiation potential. The adjuvant not only amplifies human mesenchymal stem cells rapidly to harvest the growth factor, but also maintains the characteristics of the multifunction of stem cells for the purposes of culturing and amplifying the human mesenchymal stem cells.

13 Claims, 25 Drawing Sheets

Specification includes a Sequence Listing.

10% fetal bovine serum

10% human serum

10% human serum + Adjuvant

2% human serum + Adjuvant

FIG. 9B

| | A | B | C | D | E | F | G | H | I | J | K | L |
|---|---|---|---|---|---|---|---|---|---|---|---|---|
| 1 | POS | POS | NEG | NEG | AREG | BFGF | β-NGF | EGF | EGF R | FGF-4 | FGF-6 | FGF-7 |
| 2 | | | | | | | | | | | | |
| 3 | GCSF | GDNF | GM-CSF | HB-EGF | NGF | IGFBP-1 | IGFBP-2 | IGFBP-3 | IGFBP-4 | IGFBP-6 | IGF-I | IGF-1 SR |
| 4 | | | | | | | | | | | | |
| 5 | IGF-II | M-CSF | M-CSF R | NT-3 | NT-4 | PDGF Rα | PDGF Rβ | PDGF AA | PDGF AB | PDGF BB | PlGF | SCF |
| 6 | | | | | | | | | | | | |
| 7 | SCF R | TGF-α | TGF-β1 | TGF-β2 | TGF-β3 | VEGF | VGEF R2 | VGEF R3 | VGEF-D | BLANK | BLANK | POS |
| 8 | | | | | | | | | | | | |

10% human serum (before culture) versus 10% human serum

| | A | B | C | D | E | F | G | H | I | J | K | L |
|---|---|---|---|---|---|---|---|---|---|---|---|---|
| 1 | POS | POS | NEG | NEG | AREG | BFGF | β-NGF | EGF | EGF R | FGF-4 | FGF-6 | FGF-7 |
| 2 | | | | | | | | | | | | |
| 3 | GCSF | GDNF | GM-CSF | HB-EGF | NGF | IGFBP-1 | IGFBP-2 | IGFBP-3 | IGFBP-4 | IGFBP-6 | IGF-I | IGF-1 SR |
| 4 | | | | | | | | | | | | |
| 5 | IGF-II | M-CSF | M-CSF R | NT-3 | NT-4 | PDGF Rα | PDGF Rβ | PDGF AA | PDGF AB | PDGF BB | PlGF | SCF |
| 6 | | | | | | | | | | | | |
| 7 | SCF R | TGF-α | TGF-β1 | TGF-β2 | TGF-β3 | VEGF | VGEF R2 | VGEF R3 | VGEF-D | BLANK | BLANK | POS |
| 8 | | | | | | | | | | | | |

10% human serum versus 10% human serum + Adjuvant

| | A | B | C | D | E | F | G | H | I | J | K | L |
|---|---|---|---|---|---|---|---|---|---|---|---|---|
| 1 | POS | POS | NEG | NEG | AREG | BFGF | β-NGF | EGF | EGF R | FGF-4 | FGF-6 | FGF-7 |
| 2 | | | | | | | | | | | | |
| 3 | GCSF | GDNF | GM-CSF | HB-EGF | HGF | IGBFP-1 | IGBFP-2 | IGBFP-3 | IGBFP-4 | IGFBP-6 | IGF-1 | IGF-1 SR |
| 4 | | | | | | | | | | | | |
| 5 | IGF-II | M-CSF | M-CSF | NT-3 | NT-4 | PDGF Rα | PDGF Rβ | PDGF AA | PDGF AB | PDGF BB | PIGF | SCF |
| 6 | | | | | | | | | | | | |
| 7 | SCF R | TGF-α | TGF-β1 | TGF-β2 | TGF-β3 | VEGF | VGEF R2 | VGEF R3 | VGEF-D | BLANK | BLANK | POS |
| 8 | | | | | | | | | | | | |

10% fetal bovine serum ○ versus 10% fetal bovine serum (Low oxygen) ● versus 10% fetal bovine serum + Adjuvant ◍

F I G . 9 G

SEQUENCE LISTING

```
<160> NUMBER OF SEQ ID NOS: 30

<210> SEQ ID NO 1
<211> LENGTH: 18
<212> TYPE: DNA
<213> ORGANISM: Artificial Sequence
<220> FEATURE:
<223> OTHER INFORMATION: Beta-actin forward primer

<400> SEQUENCE: 1
cgccaaccgc gagaagat                                                 18

<210> SEQ ID NO 2
<211> LENGTH: 18
<212> TYPE: DNA
<213> ORGANISM: Artificial Sequence
```

```
<220> FEATURE:
<223> OTHER INFORMATION: Beta-actin reverse primer

<400> SEQUENCE: 2
cgtcaccgga gtccatca                                                 18

<210> SEQ ID NO 3
<211> LENGTH: 22
<212> TYPE: DNA
<213> ORGANISM: Artificial Sequence
<220> FEATURE:
<223> OTHER INFORMATION: Nanog forward primer

<400> SEQUENCE: 3
aatacctcag cctccagcag at                                            22

<210> SEQ ID NO 4
<211> LENGTH: 23
<212> TYPE: DNA
<213> ORGANISM: Artificial Sequence
<220> FEATURE:
<223> OTHER INFORMATION: Nanog reverse primer

<400> SEQUENCE: 4
tgcgtcacac cattgctatt ctt                                           23

<210> SEQ ID NO 5
<211> LENGTH: 18
<212> TYPE: DNA
<213> ORGANISM: Artificial Sequence
<220> FEATURE:
<223> OTHER INFORMATION: SOX2 forward primer

<400> SEQUENCE: 5
agaccagtac ccgcatct                                                 18

<210> SEQ ID NO 6
<211> LENGTH: 17
<212> TYPE: DNA
<213> ORGANISM: Artificial Sequence
<220> FEATURE:
<223> OTHER INFORMATION: SOX2 reverse primer

<400> SEQUENCE: 6
cgctccgcct cctccac                                                  17

<210> SEQ ID NO 7
<211> LENGTH: 20
<212> TYPE: DNA
<213> ORGANISM: Artificial Sequence
<220> FEATURE:
<223> OTHER INFORMATION: CXCR4 forward primer

<400> SEQUENCE: 7
cgtggaacgt ttttcctgtt                                               20

<210> SEQ ID NO 8
<211> LENGTH: 21
<212> TYPE: DNA
<213> ORGANISM: Artificial Sequence
<220> FEATURE:
<223> OTHER INFORMATION: CXCR4 reverse primer

<400> SEQUENCE: 8
tgtaggtgct gaaatcaacc c                                             21
```

<210> SEQ ID NO 9
<211> LENGTH: 37
<212> TYPE: DNA
<213> ORGANISM: Artificial Sequence
<220> FEATURE:
<223> OTHER INFORMATION: TERT forward primer

<400> SEQUENCE: 9
ggtttttgag ggtgagggtg agggtgaggg tgagggt                                37

<210> SEQ ID NO 10
<211> LENGTH: 39
<212> TYPE: DNA
<213> ORGANISM: Artificial Sequence
<220> FEATURE:
<223> OTHER INFORMATION: TERT reverse primer

<400> SEQUENCE: 10
tcccgactat ccctatccct atccctatcc ctatccta                               39

<210> SEQ ID NO 11
<211> LENGTH: 20
<212> TYPE: DNA
<213> ORGANISM: Artificial Sequence
<220> FEATURE:
<223> OTHER INFORMATION: Cbfa1 forward primer

<400> SEQUENCE: 11
tggcagcacg ctattaaatc                                                   20

<210> SEQ ID NO 12
<211> LENGTH: 20
<212> TYPE: DNA
<213> ORGANISM: Artificial Sequence
<220> FEATURE:
<223> OTHER INFORMATION: Cbfa1 reverse primer

<400> SEQUENCE: 12
tctgccgcta gaattcaaaa                                                   20

<210> SEQ ID NO 13
<211> LENGTH: 21
<212> TYPE: DNA
<213> ORGANISM: Artificial Sequence
<220> FEATURE:
<223> OTHER INFORMATION: OC forward primer

<400> SEQUENCE: 13
caaagtctaa ctagggatac c                                                 21

<210> SEQ ID NO 14
<211> LENGTH: 18
<212> TYPE: DNA
<213> ORGANISM: Artificial Sequence
<220> FEATURE:
<223> OTHER INFORMATION: OC reverse primer

<400> SEQUENCE: 14
agagatgagt ctgtcctg                                                     18

<210> SEQ ID NO 15
<211> LENGTH: 24
<212> TYPE: DNA
<213> ORGANISM: Artificial Sequence
<220> FEATURE:
<223> OTHER INFORMATION: COL IA1 forward primer

```
<400> SEQUENCE: 15
gactctaaga tcagagacgg agac                                              24

<210> SEQ ID NO 16
<211> LENGTH: 24
<212> TYPE: DNA
<213> ORGANISM: Artificial Sequence
<220> FEATURE:
<223> OTHER INFORMATION: COL IA1 reverse primer

<400> SEQUENCE: 16
tcgctgacat ctccattcat tcac                                              24

<210> SEQ ID NO 17
<211> LENGTH: 21
<212> TYPE: DNA
<213> ORGANISM: Artificial Sequence
<220> FEATURE:
<223> OTHER INFORMATION: ACAN forward primer

<400> SEQUENCE: 17
tacactggcg agcactgtaa c                                                 21

<210> SEQ ID NO 18
<211> LENGTH: 20
<212> TYPE: DNA
<213> ORGANISM: Artificial Sequence
<220> FEATURE:
<223> OTHER INFORMATION: ACAN reverse primer

<400> SEQUENCE: 18
cagtggccct ggtacttgtt                                                   20

<210> SEQ ID NO 19
<211> LENGTH: 22
<212> TYPE: DNA
<213> ORGANISM: Artificial Sequence
<220> FEATURE:
<223> OTHER INFORMATION: COL IIA1 forward primer

<400> SEQUENCE: 19
gaatagcacc attgtgtagg ac                                                22

<210> SEQ ID NO 20
<211> LENGTH: 17
<212> TYPE: DNA
<213> ORGANISM: Artificial Sequence
<220> FEATURE:
<223> OTHER INFORMATION: COL IIA1 reverse primer

<400> SEQUENCE: 20
aatgccccct gagtgac                                                      17

<210> SEQ ID NO 21
<211> LENGTH: 23
<212> TYPE: DNA
<213> ORGANISM: Artificial Sequence
<220> FEATURE:
<223> OTHER INFORMATION: PPAR-Gamma forward primer

<400> SEQUENCE: 21
ttgctgtcat tattctcagt gga                                               23

<210> SEQ ID NO 22
```

<210> SEQ ID NO 22
<211> LENGTH: 20
<212> TYPE: DNA
<213> ORGANISM: Artificial Sequence
<220> FEATURE:
<223> OTHER INFORMATION: PPAR-Gamma reverse primer

<400> SEQUENCE: 22
gaggactcag ggtggttcag                                           20

<210> SEQ ID NO 23
<211> LENGTH: 19
<212> TYPE: DNA
<213> ORGANISM: Artificial Sequence
<220> FEATURE:
<223> OTHER INFORMATION: aP2 forward primer

<400> SEQUENCE: 23
gacatcagcg cctacatcg                                            19

<210> SEQ ID NO 24
<211> LENGTH: 18
<212> TYPE: DNA
<213> ORGANISM: Artificial Sequence
<220> FEATURE:
<223> OTHER INFORMATION: aP2 reverse primer

<400> SEQUENCE: 24
ggctgtgctg gaacaggt                                             18

<210> SEQ ID NO 25
<211> LENGTH: 18
<212> TYPE: DNA
<213> ORGANISM: Artificial Sequence
<220> FEATURE:
<223> OTHER INFORMATION: IGF-1 forward primer

<400> SEQUENCE: 25
aagatgcaca ccatgtcc                                             18

<210> SEQ ID NO 26
<211> LENGTH: 20
<212> TYPE: DNA
<213> ORGANISM: Artificial Sequence
<220> FEATURE:
<223> OTHER INFORMATION: IGF-1 reverse primer

<400> SEQUENCE: 26
tgttgaaata aaagcccctg                                           20

<210> SEQ ID NO 27
<211> LENGTH: 21
<212> TYPE: DNA
<213> ORGANISM: Artificial Sequence
<220> FEATURE:
<223> OTHER INFORMATION: HGF forward primer

<400> SEQUENCE: 27
tgttcccttt tttgggtaag c                                         21

<210> SEQ ID NO 28
<211> LENGTH: 20
<212> TYPE: DNA
<213> ORGANISM: Artificial Sequence
<220> FEATURE:
<223> OTHER INFORMATION: HGF reverse primer

<400> SEQUENCE: 28

```
cccatttgcc acagaaagtt                                                    20

<210> SEQ ID NO 29
<211> LENGTH: 23
<212> TYPE: DNA
<213> ORGANISM: Artificial Sequence
<220> FEATURE:
<223> OTHER INFORMATION: EGF forward primer

<400> SEQUENCE: 29
ctaatcacct actcaatgcc tgg                                                23

<210> SEQ ID NO 30
<211> LENGTH: 25
<212> TYPE: DNA
<213> ORGANISM: Artificial Sequence
<220> FEATURE:
<223> OTHER INFORMATION: EGF reverse primer

<400> SEQUENCE: 30
tgattctccc agtactctta cttgg                                              25
```

ADJUVANT FOR RAPID PROLIFERATION OF HUMAN MESENCHYMAL STEM CELLS IN VITRO, METHOD FOR RAPID PROLIFERATION OF HUMAN MESENCHYMAL STEM CELLS IN VITRO, METHOD FOR GROWTH FACTOR HARVESTED FROM RAPID PROLIFERATION OF HUMAN MESENCHYMAL STEM CELLS IN VITRO AND USE THEREOF

FIELD OF THE INVENTION

The present invention relates to an adjuvant for rapid proliferation of human mesenchymal stem cells in vitro, in particular to the adjuvant containing an antioxidant and a growth factor added into a medium of human mesenchymal stem cells to proliferate human mesenchymal stem cells at primary culture or subculture to obtain the growth factor.

BACKGROUND OF THE INVENTION

At present, the scientific community has defined "stem cell" and its properties as follows. The stem cell refers to a cell with self-renewal and proliferation capability as well as the property of maintaining an undifferentiated status for a long time, and after the cell is induced and simulated appropriately, the cell can be differentiated into cell groups of different lineages and achieves a multi-differentiation of tissues with specific functions.

Based on the source and differentiation potential of the stem cell, the stem cell can be categorized into the following types:

1. Totipotent stem cell: It has the ability to be developed into a complete and independent living organism such as a zygote or an embryo and developed to a cell group of approximately eight cell stages.

2. Pluripotent stem cell: Approximately four days after a zygote is fertilized, the pluripotent stem cell starts entering into a blastocyst period, and the blastocyst can be divided into two parts: an outer layer of cells and an inner cell mass. In the development process of the embryo, the outer layer of cells will form placenta and fetus attached onto the required supporting tissues in the uterus, and the inner cell mass will form ectoderm, mesoderm and endoderm, each being divided into different systems and organs. Although the inner cell mass has the ability of forming various parts of human body, yet external supporting systems and environments for the growth of the placenta and fetus cannot be formed if the inner cell mass without the outer layer of cells is placed into the uterus of a healthy mature female, and a complete individual cannot be developed. Therefore, the multifunction ability still has partial limitations.

3. Multipotent stem cell: This is the most extensively studied stem cell, and the multipotent stem cell is differentiated downwardly from the pluripotent stem cell and capable of becoming the stem cell of specific tissues such as a hematopoietic stem cell and a mesenchymal stem cell, wherein the hematopoietic stem cell comes from peripheral blood, umbilical cord blood and marrow and can be divided into various blood corpuscles and lymphs, and the mesenchymal stem cell comes from adipose, periosteum, synovial membrane, marrow and mesenchymal tissue of a certain organ such as the placenta. For example, the hematopoietic stem cell can be a hematopoietic stem cell which can be differentiated into a lymph stem cell and a marrow stem cell, wherein the lymph stem cell can be differentiated into a lymphocyte, a killer cell, etc, and the bone marrow stem cell can be differentiated into a red blood corpuscle, a white blood corpuscle, a blood platelet, etc. The multipotent stem cell can be found in a body of both adult and child, and the self-regeneration ability of the stem cell plays an important role of supplying and refreshing the cells normally consumed in our body. At present, the already separated multipotent stem cells include brain, retina, bone marrow, liver, skeletal muscle, skin, umbilical cord, umbilical cord blood, adipose tissue, etc.

4. Unipotent stem cell: It generally refers to a stem cell with the ability of differentiating into a specific kind of tissue or is called a progenitor cell, and the cells of this sort generally exist in the tissues of each part of the body, and the most easily found stem cell is a liver progenitor cell, and nerve progenitor cell.

The mesenchymal stem cell was first academically defined as a colony-forming unit of fibroblast (CFU-Fs). In the culture process, a single layer of the mesenchymal stem cell is attached onto a surface of the plastic Petri dish, and in a form similar to fibroblast and in a spindle shape. This kind of stem cells will be proliferated rapidly in vitro to form a colony, and has a potential of differentiating into osteoblast, adipocyte, and chondrocyte. In recent years, researches indicate that this cell can be differentiated into hepatocyte, cardiomyocyte, neural cell, islet cell, etc (Minguell et al., 2001).

The source of the mesenchymal stem cell comes from the separation of various different tissues of a human body. For example, an adipose tissue obtained from direct surgical excision or obtained from liposuction is a rich source of stem cells, and the adipose tissue-derived stem cell (ADSCs) has the following advantages: low invasiveness, little harm to human body, high producing quantity at a time, and proliferation and culture in vitro, etc. In addition, the adipose tissue-derived stem cell also has the potential to differentiate into bone, cartridge, muscle and adipocyte (Zuk et al., 2002), so that the adipose tissue-derived stem cell is considered to be one of the stem cells with high development potential.

Regardless of fundamental medical research or clinical treatment, the research and application of stem cells require a sufficient number of cells and a culture in an appropriate environment including a stimulation such as an appropriate microenvironment or growth factor to prevent the stem cell from being aged before the proliferation and culture process, losing activity or differentiating into other cells. However, the difference including the cell separation technology, growth medium and culture condition causes a significant difference of proliferation and differentiation power of the stem cell (Pittenger et al., 2008). In addition, many journals reported the tendency of having an ageing issue of the mesenchymal stem cell in the culture and proliferation processes (Bonab et al., 2006; Shibata et al., 2007; Wagner et al., 2008). Therefore, the differences of performance and ageing of the cells in a proliferation of the stem cell probably hinder the clinical use of the mesenchymal stem cell. It is a major subject for scientist to culture the stem cell rapidly and effectively and amplify its number, while maintaining the undifferentiated status and reduce the ageing phenomenon, and having the multifunctional feature.

In recent years, researches reported and pointed out that a large quantity of paracrine factors such as a vascular endothelial growth factor (VEGF), an insulin-like growth factor 1 (IGF-I), an epidermal growth factor (EGF), a keratinocyte growth factor (KGF), angiopoietin-1, stromal-derived factor-1, macrophage inflammatory protein-1α, macrophage inflammatory protein-1β, and erythropoietin capable of promoting wound healing existed in a conditional medium of the cultured bone marrow mesenchymal stem cell (BMMSC) (Martin et al., 1997). The adipose tissue-derived stem cell (ADSC) has been shown that its gene expression and phenotype have no significant difference from those of the bone marrow mesenchymal stem cell, umbilical cord blood mesenchymal stem cell, periosteum mesenchymal stem cell, synoval mesenchymal stem cell and muscle mesenchymal stem cell (Sheehy et al., 2012; Hung et al., 2012; Hung et al., 2007). In view of the adipose tissue-derived stem cell has a better separation and in vitro proliferation condition than the bone marrow mesenchymal stem cell, and has a good chance to be applied in wound repair and regeneration. At present, the adipose tissue-derived stem cell in the conditional medium secretes the following growth factors, such as basic fibroblast growth factor (bFGF), keratinocyte growth factor (KGF), transformation growth factor (TGF-β), hepatocyte growth factor (HGF), vascular endothelial growth factor (VEGF), etc, and these growth factors may be related to wound healing. Therefore, it is a worthy research subject to proliferate mesenchymal stem cells and produce a large quantity of growth factors rapidly.

R.O.C. Pat. No. 201331366 entitled "In vitro serum-free somatic stem cell stem cell culture amplification technology" provides an in vitro serum-free somatic stem cell stem cell, and a method of plasma rich growth factor (PRGF) in serum-free stem cell culture liquid to perform primary culture and subculture in human somatic stem cell, and after the human somatic stem cell cultured by this method is subcultured for several times, the human somatic stem cell still maintains at a substantially undifferentiated status. However, the quantity of stem cells obtained by such culture method is approximately equal to 55,000 of cells/cm$^2$ before the cells are subcultured to the third passage (P3). If it is necessary to obtain more stem cells, more culture days and more passages of subculture are required, thus the stem cells are exposed to more risk of contamination for a greater number of subcultures.

R. O. C. Pat. No. 201118172 entitled "Method of amplifying mesenchymal stem cells in low-density and low-oxygen culture" can increase human mesenchymal stem cells in the condition without affecting the cell proliferation to rapidly and effectively increase the proliferation in vitro, reduce the potential of ageing, and increase the potential of differentiation. However, the incubator of culturing cell used by most research organizations just provides the function of differentiating the pressure of carbon dioxide and adjusting the moisture. If it is necessary to culture in a low oxygen environment, the incubator with the oxygen pressure adjustment functions is relatively unaffordable by research organizations without sufficient research budgets.

R.O.C. Pat. No. 201231087, entitled "Manufacturing procedure of a maintenance product including a plurality of growth factors", and the method comprises the steps of taking out a healthy adipose; mixing a predetermined volume of solvent into the adipose tissue to clean the adipose tissue; adding a predetermined dosage of reagent into a predetermined volume of adipose tissue and performing a centrifugal separation; the produced and separated adipose tissue is mixed into a predetermined dosage of enzyme into an eppendorf to vibrate the eppendorf; producing a precipitate for a cell culture to produce a somatic cell; and after obtaining the somatic cell, and the cell culture liquid produced by the aforementioned culture method contains a growth factor (such as VEGF, HGF, b-FGF, TGF, and IGF) for cell secretion to complete the raw material of high-performance of maintenance product. However, the culture method is to put the somatic cells into a basic medium DMEM (Dulbecco's Modified Eagle Medium) containing a 10% fetal bovine serum (10% FBS) for the culture, and the slow proliferation rate of somatic cells, so that the quantity of the secreted growth factor is relatively little. If it is necessary to obtain a large quantity of growth factor, a greater number of culture days and a greater number of passages of subculture must required, and thus the stem cells are exposed to more risk of contamination for a greater number of subcultures.

In summation of the description above, the multifunctional characteristic of the stem cell can be maintained to proliferate the in vitro human mesenchymal stem cells rapidly, while obtaining a large quantity of growth factor secreted from the human mesenchymal stem cells by using a human mesenchymal stem cells culture adjuvant and a culture method thereof, so as to rapidly and efficiently amplify the number of cells and obtain a large quantity of growth factors.

SUMMARY OF THE INVENTION

In view of the drawbacks of the conventional human mesenchymal stem cell culture for amplifying the number of cells and obtaining the growth factor secreted from the human mesenchymal stem cells, the inventor of the present invention conducted extensive researches and experiments and provided an adjuvant for rapid proliferation of human mesenchymal stem cells in vitro and its culture method and a method of amplifying human mesenchymal stem cells in vitro rapidly to obtain the growth factor and its use, in hope of achieving the effect of amplifying the human mesenchymal stem cells rapidly and effective to obtain the growth factor.

To achieve the aforementioned objectives, the present invention provides an adjuvant for rapid proliferation of human mesenchymal stem cells in vitro, and the method comprises at least one antioxidant and a basic fibroblast growth factor (FGF-2).

Wherein, the human mesenchymal stem cell is one selected from the group consisting of an adipose tissue-derived stem cell, a bone marrow mesenchymal stem cell and an umbilical cord mesenchymal stem cell.

Wherein, the antioxidant comprises a combination of a long-acting ascorbic acid derivative and an N-acetyl-L-cysteine (NAC).

Wherein, the long-acting ascorbic acid derivative is a L-ascorbic acid-2-phosphate (AsA2P).

Wherein, the concentration of basic fibroblast growth factor (FGF-2) is 1 nanogram/liter (ng/mL) to 20 ng/mL.

Wherein, by inhibiting the cyclin-dependent kinase inhibitors: p21 and p27 proteins expression to improve the expression of the cyclin-dependent kinase-2 (CDK-2), the cyclin-dependent kinase-4 (CDK-4), and the cell division cycle protein (CDC2).

The present invention provides a method for rapid proliferation of human mesenchymal stem cells in vitro, and the method comprises the step of adding an adjuvant into a medium including human mesenchymal stem cells to amplify human mesenchymal stem cells to obtain substantially undifferentiated human mesenchymal stem cells.

Wherein, the medium is containing a serum additive.

Wherein, the serum additive is a human serum or a fetal bovine serum with a volume percent concentration from 2% to 10%.

Wherein, the method for rapid proliferation of human mesenchymal stem cells in vitro further comprises the step of cryopreservating the amplified human mesenchymal stem cell for a further use.

Wherein, the step of cryopreservating the amplified human mesenchymal stem cell is to create a cell bank.

Wherein, the method for rapid proliferation of human mesenchymal stem cells in vitro comprises carrying out an extraction step to obtain a cell extract of the human mesenchymal stem cell.

Wherein, the method for rapid proliferation of human mesenchymal stem cells in vitro further executes an induction and differentiation step to obtain a cell differented from the human mesenchymal stem cell.

Wherein, the cell differented from the human mesenchymal stem cell includes a cell selected from the group consisting of a osteogenic cell, an adipocyte and a chondrocyte.

The present invention further provides a medical composition comprising a substantially undifferented human mesenchymal stem cell obtained by the aforementioned method for rapid proliferation of human mesenchymal stem cells in vitro or a cell differented from the human mesenchymal stem cell.

Wherein, the medical composition is combined with a biocompatible material and used for regenerative medicine or tissue engineering.

The present invention provides a method of amplifying human mesenchymal stem cells rapidly to obtain a growth factor in vitro. After the method for rapid proliferation of human mesenchymal stem cells in vitro is applied for culture, at least a growth factor is harvested from the medium.

Wherein, the growth factors include: FGF-2, EGF, FGF-4, FGF-6, FGF-7, HB-EGF, HGF, IGFBP-1, IGFBP-2, IGFBP-3, IGFPB-4, IGFBP-6, IGF-I, IGF-I SR, IGF-II, M-CSF, M-CSF R, PDGF Rα, PDGF-Rβ, PDAF-AA, PDGF-AB, PDGF-BB, PlGF, SCF, TGF-β3, VEGF, or VEGF R2.

The present invention provides a growth factor obtained from the aforementioned method for growth factor harvested from rapid proliferation of human mesenchymal stem cells in vitro.

The present invention provides a medical composition comprising a growth factor harvested from the aforementioned method for growth factor harvested from rapid proliferation of human mesenchymal stem cells in vitro.

The present invention provides a use of a medicine manufactured by the aforementioned growth factor for promoting wound healing or serving as a skin care product.

The advantages and effects of the present invention are described below:

1. Rapid Proliferation: The adjuvant for rapid proliferation of human mesenchymal stem cells in vitro of the present invention is added into a medium to increase the percentage of having the synthesis cycle (S phase) of the cell cycle of the human mesenchymal stem cell occurred at the first passage or subculture, so as to promote rapid cell division and proliferation while maintaining the potential of multi-functional differentiation of the stem cell.

2. Reduction of Cell Ageing: The adjuvant for rapid proliferation of human mesenchymal stem cells in vitro of the present invention is added into a medium to increase the telomerase reverse transcriptase (TERT) of the human mesenchymal stem cell to extend the time of the telomere reducing to retard the ageing of cells and extend the life of the cells.

3. Harvest of a Large Quantity of Growth Factor Rapidly: The adjuvant for rapid proliferation of human mesenchymal stem cells in vitro of the present invention is added into a medium to obtain at least two to three times of the content of a growth factor such as insulin-like growth factor-1 (IGF-1), hepatocyte growth factor (HGF) and epidermal growth factor (EGF) from a fetal bovine serum with a volume percent concentration equal to 10%, when compared with the conventional culture.

4. Reduction of Pathogenic Contamination: The adjuvant for rapid proliferation of human mesenchymal stem cells in vitro of the present invention used together with the human serum for a culture avoids using allogenic or heterologous serum for the culture to minimize the risk of pathogenic cross contamination between allogenic or heterologous serums.

BRIEF DESCRIPTION OF THE DRAWINGS

FIG. 9B shows the comparisons of the cytokine array analysis of the present invention as depicted in FIG. 9A;

FIG. 9G shows the cytokine array analysis results of FIG. 9F in accordance with the present invention;

DESCRIPTION OF THE PREFERRED EMBODIMENTS

Figure 1A:
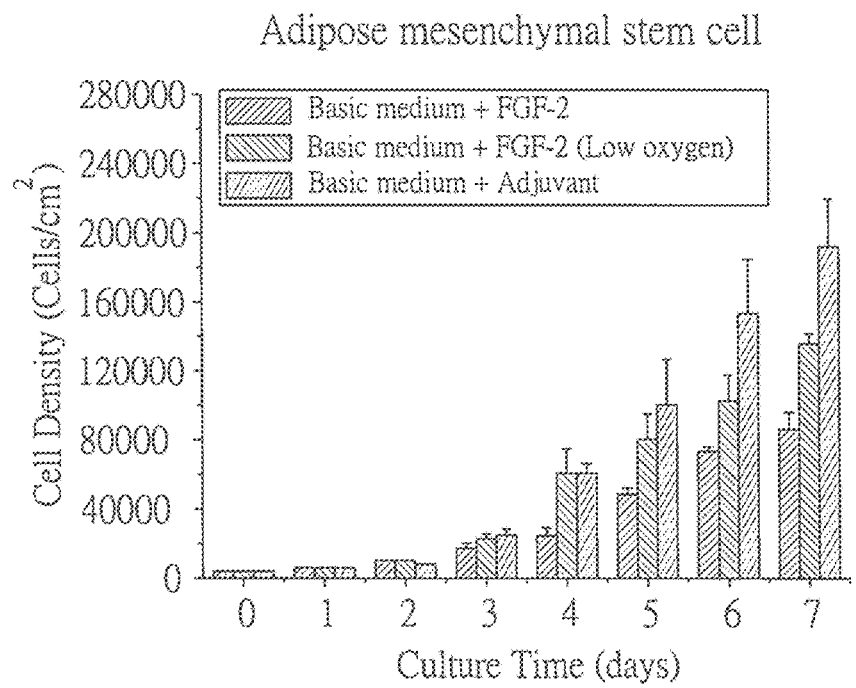
FIGS. 1A to 1C are cell density versus culture time graphs of human mesenchymal stem cells at different culture conditions respectively in accordance with the present invention.

The present invention will become clearer in light of the following detailed description of an illustrative embodiment of this invention described in connection with the drawings. It is intended that the embodiments and drawings disclosed herein are to be considered illustrative rather than restrictive.

The present invention provides an adjuvant for rapid proliferation of human mesenchymal stem cells in vitro, comprising at least one antioxidant and a basic fibroblast growth factor (FGF-2), wherein the antioxidant includes a combination of a long-acting ascorbic acid derivative and a N-acetyl-L-cysteine (NAC). Preferably, the long-acting ascorbic acid derivative is a L-ascorbic acid-2-phosphate (AsA2P), and the basic fibroblast growth factor (FGF-2) has a concentration from 1 to 20 nanogram/milliliter.

Preferably, the human mesenchymal stem cell is one selected from the group consisting of an adipose tissue-derived stem cell, a bone marrow mesenchymal stem cell and an umbilical cord mesenchymal stem cell.

Preferably, the adjuvant for rapid proliferation of human mesenchymal stem cells in vitro of the present invention by inhibiting the expression of the cyclin-dependent kinase inhibitors: p21 and p27 proteins in the human mesenchymal stem cell to improve the expression of a cyclin-dependent kinase-2 (CDK-2), a cyclin-dependent kinase-4 (CDK-4) and a cell division cycle protein (CDC2), so as to increase the percentage of promoting the cell cycle to enter into a synthesis phase (S phase) and divide and proliferate the cells rapidly.

The present invention further provides a method for rapid proliferation of human mesenchymal stem cells in vitro, comprising the step of adding the adjuvant into a medium containing the human mesenchymal stem cells for a culture to amplify the human mesenchymal stem cells in order to harvest substantially undifferentiated human mesenchymal stem cells.

Preferably, the medium is containing a serum additive.

Preferably, the serum additive is a human serum or fetal bovine serum with a volume percent concentration from 2% to 10%.

Preferably, the method for rapid proliferation of human mesenchymal stem cells in vitro further comprises the step of executing an extraction step to obtain a cell extract of the human mesenchymal stem cells.

Preferably, the method for rapid proliferation of human mesenchymal stem cells in vitro further comprises cryopreservation step of amplifying the human mesenchymal stem cell for further use.

Preferably, the term "cryopreservation" generally refers to a method of adding a cryoprotectant such as dimethyl sulfoxide (DMSO) or glycerin into a cell and then cooling and storing it at a temperature below zero such as −80☐ or −196☐ (which is the boiling point of liquid nitrogen). The method and process of the cryopreservation are prior arts, and thus will not be described in details (refer to Basic Cell Culture Protocol, $2^{nd}$ Edition (1997) edited by Pollard, J. W. and Walker, J. M. and published by Humma Press; and Culture of Animal Cell, $4^{th}$ Edition (2000) authored by Freshney, R. I. and published by Wiley-Liss).

The present invention provides a cell bank comprising the human mesenchymal stem cells amplified by the cryopreservation in accordance with the aforementioned method for rapid proliferation of human mesenchymal stem cells in vitro.

Preferably, the method for rapid proliferation of human mesenchymal stem cells in vitro further comprises an induction and differentiation step to obtain a cell differentiated from the aforementioned human mesenchymal stem cell.

Preferably, the cell differentiated from the aforementioned human mesenchymal stem cells includes a osteogenic cell, an adipocyte or a chondrocyte.

The present invention further provides a medical composition comprising a substantially undifferentiated human mesenchymal stem cell or a cell differentiated from the aforementioned human mesenchymal stem cell obtained by the aforementioned method for rapid proliferation of human mesenchymal stem cells in vitro.

Preferably, the medical composition includes the aforementioned human mesenchymal stem cell, a cell differentiated from the human mesenchymal stem cell, a cell secretion, a cell extract or any combination of the above and an acceptable carrier/excipient of an appropriate treatment. Wherein, the cell secretion can be obtained after the purification and concentration of a cell medium in other preferred embodiments.

Further, the medical composition combined with a biocompatible material is applied for regenerative medicine or tissue engineering.

The present invention further provides a method of obtaining a growth factor by an adjuvant for rapid proliferation of human mesenchymal stem cells in vitro, and then cultured by the aforementioned method for rapid proliferation of human mesenchymal stem cells in vitro. During the fast proliferation of the cell, various types of growth factors of the cell are secreted in the medium, so that the aforementioned growth factors can be obtained in the medium. Wherein, the growth factors include FGF-2, EGF, FGF-4, FGF-6, FGF-7, HB-EGF, HGF, IGFBP-1, IGFBP-2, IGFBP-3, IGFPB-4, IGFBP-6, IGF-I, IGF-I SR, IGF-II, M-CSF, M-CSF R, PDGF Rα, PDGF-Rβ, PDAF-AA, PDGF-AB, PDGF-BB, PlGF, SCF, TGF-β3, VEGF, and VEGF R2.

The present invention provides a growth factor harvested by the aforementioned method for growth factor harvested from rapid proliferation of human mesenchymal stem cells in vitro.

The present invention provides a medical composition comprising the growth factor harvested by the aforementioned method for growth factor harvested from rapid proliferation of human mesenchymal stem cells in vitro, but the growth factor is not limited to the use of healing skin wounds.

The present invention provides a medical use of the aforementioned growth factor for preparing the medicine for promoting wound healing or serving as a skin care product.

The present invention provides a skin care product including the aforementioned growth factor for repairing skin sunburns or retarding skin cell ageing.

The human mesenchymal stem cell of the present invention refers to any cell of a human mesenchymal tissue having unlimited self-refreshing capability and can be differentiated into various cells or tissues. The human mesenchymal stem cell is a cell including but not limited to an adipose tissue-derived stem cell, a bone marrow mesenchymal stem cell, an umbilical cord mesenchymal stem cell, an umbilical cord blood mesenchymal stem cell, a periosteum mesenchymal stem cell, a synovial mesenchymal stem cell, or a muscle mesenchymal stem cell. In a preferred embodiment of the present invention, a human adipose tissue-derived stem cell is used as an example for illustrating the present invention, but the present invention is not limited to this embodiment only.

Experiment 1: Effect of the adjuvant of the present invention on the cell growth of different human mesenchymal stem cells cultured in normal oxygen environment and low oxygen environment.

1. Separation and Culture of Human Mesenchymal Stem Cells In Vitro

This experiment was conducted with the approval of the Internal Review Board (IRB100-102) of Buddhist Tzu Chi General Hospital, and human adipose tissue, umbilical cord and marrow tissue are used as the sources of stem cells, but the separation method of the human mesenchymal stem cells is a prior art and thus will not be described in details. The main purpose is to obtain the human mesenchymal stem cells to perform a primary culture. The cell culture conditions of this experiment are divided into three groups: a culture group using a basic medium with FGF-2 in a normal oxygen environment, a culture group using a basic medium with FGF-2 in a low oxygen environment, and a culture group using a basic medium with the adjuvant of the present invention in a normal oxygen environment, wherein the so-called normal oxygen environment refers to a partial pressure of oxygen approximately equal to 21%, and the low oxygen environment refers to a partial pressure of oxygen approximately equal to 5%. The basic medium is an Iscove's modified Dulbecco's medium, GIBCO-Invitrogen (IMDM) added with 10% fetal bovine serum (FBS, MSC-Qualified, GIBCO-Invitrogen) and 2 mM L-glutamine, GIBCO-Invitrogen; and the aforementioned growth factor FGF-2 has a concentration of 10 ng/mL (R&D Systems), and the adjuvant of the present invention includes 2 mM N-acetyl-L-cysteine (NAC, Sigma) and 0.2 mM AsA2P (Sigma). In each group of stem cells, the cells with a cell density of 3000 cells/cm$^2$ are cultured in 6-well plates (Becton Dickinson), and all cells are cultured at in an incubator (Forma Series II Model 3110, Thermo) with the environment of a temperature of 37 degrees Celsius, a partial pressure of carbon dioxide approximately equal to 5% and a humidity of 95%, and the medium is changed once every three days. In another culture experiment with a low oxygen culture environment, the experiment takes place in another incubator (MCO-18M, Sanyo). The effects of different human mesenchymal stem cells at different culture conditions on the cell proliferation are observed for 7 days.

1.1 Cell Growth Density Analysis

Each group of stem cells is cleaned once by a phosphate buffer solution (PBS), and then reacted with a Trypsin-EDTA solution at 37 degrees Celsius for 5 minutes, and then the cell spatula is used to remove incompletely reacted cells carefully, and the same proportion of a medium containing fetal bovine serum is used for neutralizing the enzyme activity of trypsin. The number of cells is measured by a cell counter (Vi-CELL AS, Beckman Coulter). The survived cell is distinguished from a dead cell by using 0.4% Trypan-blue (GIBCO-Invitrogen). In the calculation, the parameter settings for determining the survival rate of the mesenchymal stem cell include 100 images, Size 10-30 microns, 75% spot brightness, and 5% spot area. Each set of experiment data is measured for three times, and the result is expressed in term of mean±standard deviation.

1.2 Experiment Result

Figure 1B:
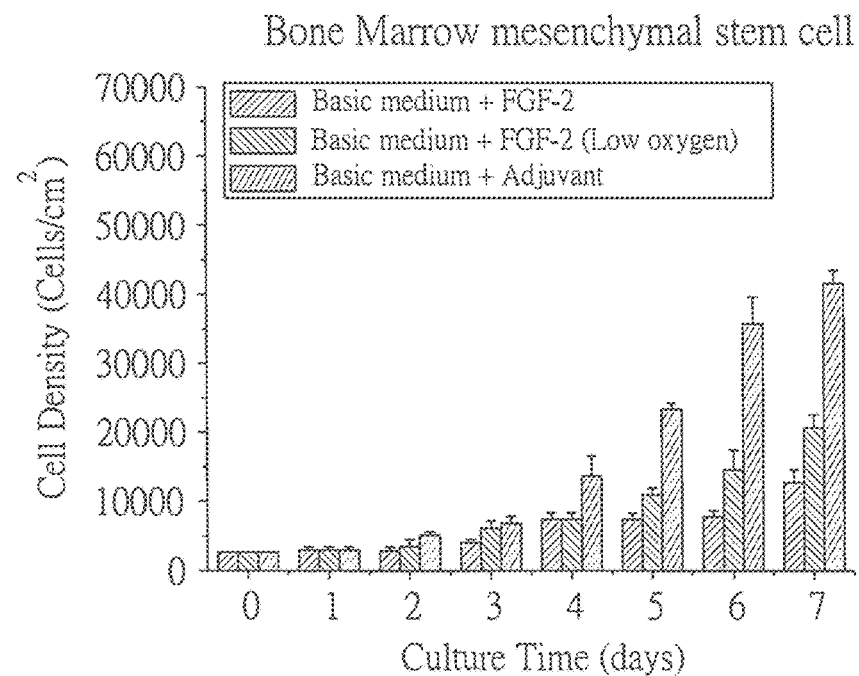
Figure 1C:
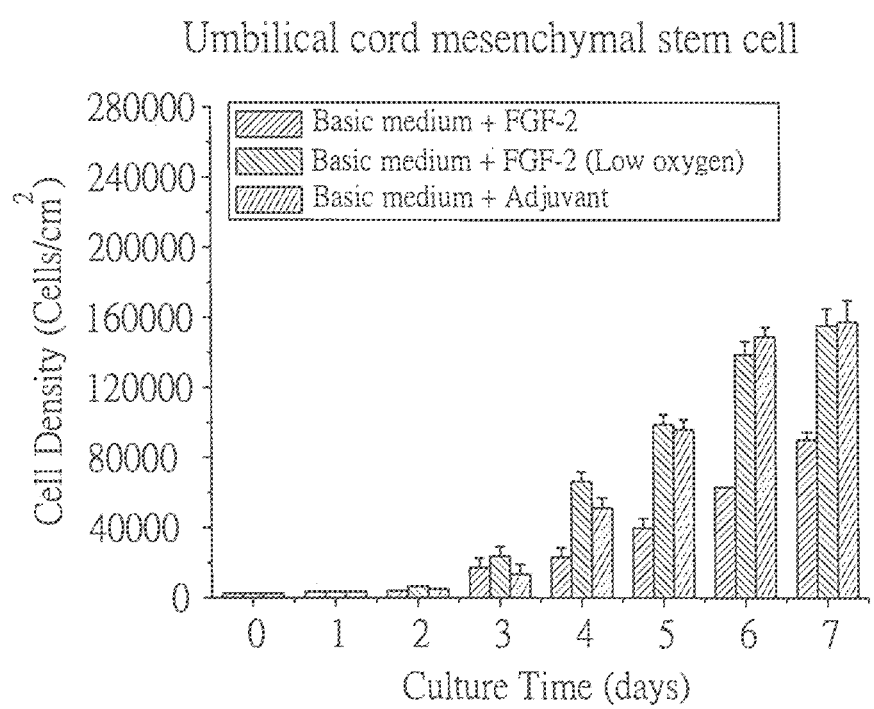

The data of the aforementioned experiment are processed by Microsoft Excel t-test statistical analysis, wherein the level of significance p<0.05, and the data are quantified in a chart. With reference to FIG. 1A for the growth of adipose-derived stem cells under three different culture conditions, the culture group of a basic medium with FGF-2 in the normal oxygen environment and the culture group of a basic medium with FGF-2 in the low oxygen environment are compared. The result shows that the stem cell is proliferated faster in a low oxygen environment, particularly the third day already has a significant difference, and the fourth day starts to be more obviously, and these observations show that the proliferation rate of the adipose tissue-derived stem cells at a low oxygen environment is better than at a normal oxygen environment. Another culture group of a basic medium with FGF-2 in a low oxygen environment and a culture group of a basic medium with the adjuvant of the present invention in a normal oxygen environment are compared. The result shows that the culture by the adjuvant of the present invention in the normal oxygen environment can have a proliferation rate close to that of the culture taken place in a low oxygen environment. Starting from the fifth day, the proliferation rate even exceeds the proliferation rate of the culture in a low oxygen environment. These results show that the addition of the adjuvant of the present invention can provide the effect of a fast proliferation when the adipose tissue-derived stem cells are cultured in the normal oxygen environment. With reference to FIGS. 1B and 1C, the same results are found in the culture experiment of the bone marrow mesenchymal stem cell or the umbilical cord mesenchymal stem cell. This experiment shows that the addition of the adjuvant of the present invention can achieve a fast proliferation while culturing the adipose tissue-derived stem cell, bone marrow mesenchymal stem cell or umbilical cord mesenchymal stem cell in the normal oxygen environment culture.

2. Cell Cycle Analysis

Each experiment group of the adipose tissue-derived stem cells are cultured at different culture conditions, and a basic medium with 10% fetal bovine serum is used as the control group, and a flow cytometer and its software (Phoenix Flow Systems) are used for detecting and analyzing a change of the cell cycle. Samples are taken after each group is cultured for three days, and the experiment for each group is repeated three times. The cells are fixed by alcohol, and DNA of the cell stained by a propidium iodide (Sigma) stain is used for analyzing the change of the cell cycle of the DNA.

2.1 Experiment Result

Figure 2A:
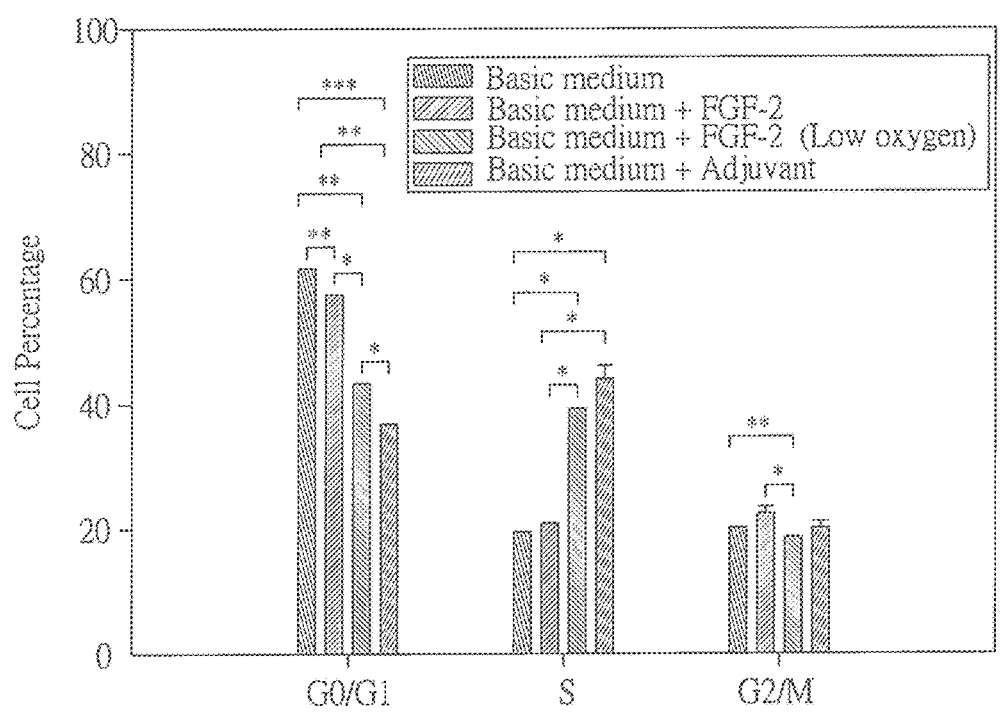
FIG. 2A is a chart showing the effect of adipose-derived stem cells cultured in different conditions in accordance with the present invention on the cell cycle.

With reference to FIG. 2A for the effect of the control group and the aforementioned three groups with different culture conditions on the cell cycle of the adipose tissue-derived stem cell, * $P<0.05$,  $P<0.01$, and * $P<0.005$. The experiment results show that the culture group with a basic medium and FGF-2 in a low oxygen environment and the culture group with a basic medium and the adjuvant of the present invention in a normal oxygen environment have a much greater percentage of the synthesis phase (S phase) when the adipose tissue-derived stem cells are situated in the cell cycle than those of the control group and the culture group with a basic medium and FGF-2 in a normal oxygen environment, and the culture group with a basic medium and FGF-2 in a low oxygen environment and the culture group with a basic medium and the adjuvant of the present invention in a normal oxygen environment have a percentage of G0/G1 phase much smaller than those of the control group and the culture group with a basic medium and FGF-2 in a normal oxygen environment, and these show that the cells cultured in a low oxygen environment or cultured by adding the adjuvant of the present invention and at a normal oxygen environment can drive the cell cycle to be situated in the synthesis phase to promote the DNA of the cells to be synthesized continuously, so as to proliferate the cells rapidly. Wherein, the percentage of the adipose tissue-derived stem cells cultured by adding the adjuvant of the present invention in a normal oxygen environment having a cell cycle situated at the synthesis phase is much greater than the culture group in the low oxygen environment, and the two have a significant difference. Therefore, the addition of the adjuvant of the present invention and the culture in a normal oxygen environment not only provides a fast proliferation, but also improves the cell proliferation rate faster than that of the culture in a low oxygen environment.

3. Western Blot Analysis for Adjusting and Controlling the Expression of Related Proteins of the Cell Cycle The conventional Western Blot uses the specific binding characteristic of antibody and antigen together with the SDS-PAGE gel electrophoresis to perform qualitative and quantitative analyses for detecting a specific protein expression, but his method is a prior art, and thus will not be described. This experiment aims at the related proteins such as Cyclin A2, Cyclin D1, Cyclin D3, CDK2, CDK4, CDK6, CDC2, p21 and p27 for adjusting and controlling the cell cycle, and the specific binding characteristic between each protein and its antibody and the aforementioned Western Blot are used for the analysis to observe the effect of the controlling and adjusting the cell cycle of the adipose tissue-derived stem cells cultured in different culture conditions on the protein expression, wherein the expression of a β-actin protein is used as the control or a basis for the standardization of quantifying each aforementioned protein expression into data. Since the β-actin protein is a protein transcribed and translated from a housekeeping gene, which is compulsory for maintaining the normal physiological phenomenon of the cells, and no significant change is resulted from various experiment conditions, therefore the β-actin protein is suitable to be used as a basis for the standardization of quantifying each aforementioned protein expression into data.

3.1 Experiment Result

Figure 2B:
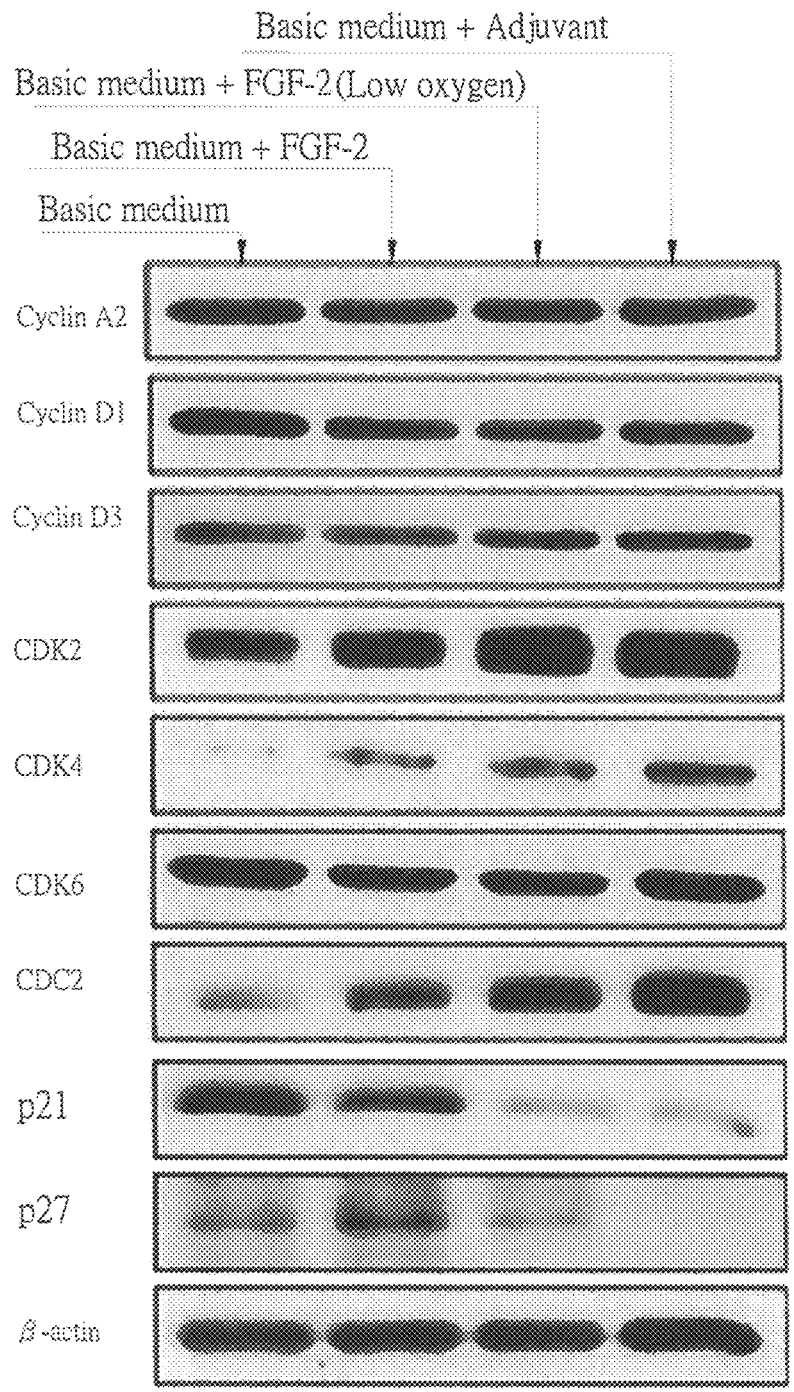
FIG. 2B is a chart showing the effect of adipose-derived stem cells cultured in different conditions in accordance with the present invention on the protein expression responsible for controlling and adjusting the cell cycle.

With reference to FIG. 2B for the expression analysis of related protein for adjusting and controlling the cell cycle of the four experiment groups of FIG. 2A, the expression of each protein is different, and reports indicate that a cyclin-dependent kinase inhibitor will inhibit the cell cycle. The expression level of cyclin-dependent kinase inhibitors: p21 and p27 proteins at the culture group with a basic medium and FGF-2 in a low oxygen environment, and the culture group with the basic medium and the adjuvant of the present invention in a normal oxygen environment are obviously lower than those of the control group, and the culture group with a basic medium and FGF-2 in a normal oxygen environment. The expression level of the p21 and p27 proteins of the culture group with the basic medium and the adjuvant of the present invention in a normal oxygen environment is approximately equal to or smaller than that of the culture group with the basic medium and FGF-2 in a low oxygen environment. In addition, the expression of the cyclin-dependent kinase-2 (CDK-2), cyclin-dependent kinase-4 (CDK-4) and cell division cycle protein (CDC2) at the culture group with the basic medium and FGF-2 in a low oxygen environment and the culture group with the basic medium and the adjuvant of the present invention in a normal oxygen environment are obviously greater than the expression of the aforementioned control group, and the culture group with the basic medium and FGF-2 in a normal oxygen environment. Even the expression level of CDK-2, CDK-4 and CDC2 proteins in the culture group with the basic medium and the adjuvant of the present invention in a normal oxygen environment is approximately equal to or greater than that of the culture group with the basic medium and FGF-2 in the low oxygen environment. Therefore, the addition of the adjuvant of the present invention in a normal oxygen environment achieves a fast proliferation for culturing the adipose tissue-derived stem cells by inhibiting the expression of the p21 and p27 proteins to improve the expression of the CDK-2, CDK-4 and CDC2 proteins, so as to duplicate and divide the cells rapidly and achieve the fast proliferation effect.

4. Relative Telomere Length Analysis

In a cell, a chromosome structure is formed by DNA, and a telomere is a repetitive DNA sequence at an end of the chromosome for protecting the integrity of the chromosome. Before the cell is divided, the chromosome is duplicated, and the telomere will be shorten a little for each time of the DNA duplication. Until the telomere is reduced to a certain extent, the stability of the chromosome cannot be maintained anymore, and the cell will die finally. Therefore, the telomere length can be used to estimate the age of a cell. After the four groups of adipose tissue-derived stem cells including the aforementioned three groups with different culture conditions and the aforementioned control group (including a basic medium containing 10% fetal bovine serum) have been cultured for 14 days, a technical method (Cawthon, 2002) reported by journals is used to measure the relative telomere length (T/S ratio) and observe the effect of different culture conditions on the telomere of the adipose tissue-derived stem cell.

4.1 Experiment Result

Figure 3:
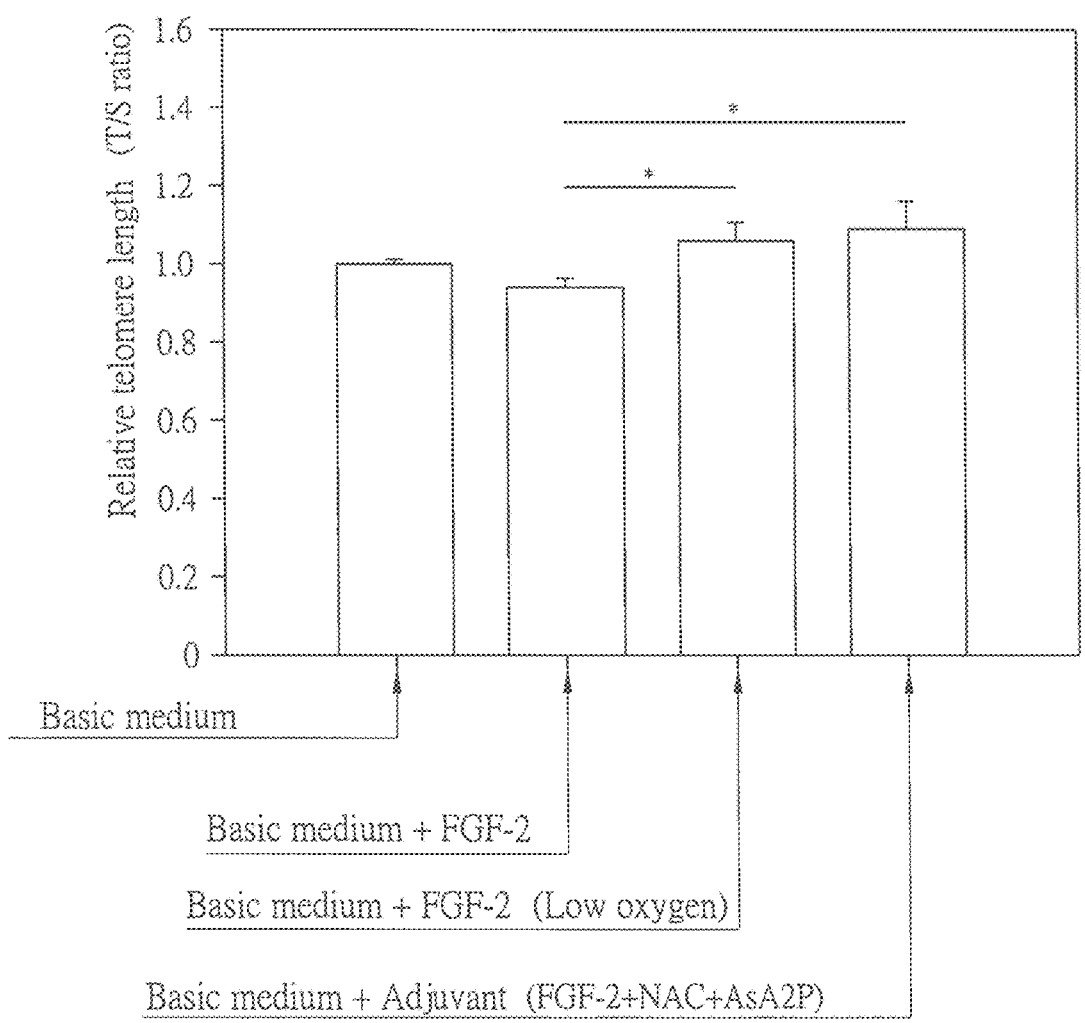
FIG. 3 is a chart showing the effect of adipose-derived stem cells cultured in different conditions in accordance with the present invention on the length of telomere of the cell.

With reference to FIG. 3 for the method of measuring the cell telomere length (T/S ratio) to obtain the aforementioned four experiment group at the culture conditions, the T/S ratio of the cell telomere has * $P<0.05$. The result shows that when the control group acts as a standard, the culture group with the basic medium and FGF-2 in a low oxygen environment and the culture group with the basic medium and the adjuvant of the present invention in a normal oxygen environment are improved than the culture group with the basic medium and FGF-2 in a normal oxygen environment and have a significant difference. Therefore, the culture in the low oxygen environment or the culture with the addition of the adjuvant of the present invention in the normal oxygen environment can improve the telomere length ratio, so as to achieve the effect of retarding the cell ageing.

5. The Effect of Normal Oxygen or High Oxygen Environment for the Culture of Adipose Tissue-Derived Stem Cell In this experiment, the culture conditions are divided into four groups, respectively: a culture group with a basic medium and FGF-2 in a normal oxygen environment, a culture group with a basic medium and FGF-2 in a high oxygen environment, a culture group with a basic medium and the adjuvant of the present invention in a normal oxygen environment, and a culture group with a basic medium and the adjuvant of the present invention in a high oxygen environment, wherein the high oxygen environment refers to a partial pressure of oxygen approximately equal to 37.5%, and parameters of the culture conditions (such as a basic medium, an incubator and a cell culture density) are the same as described in Section 1 of the aforementioned Experiment 1.

5.1 Cell Growth Density Analysis of Adipose Tissue-Derived Stem Cell

The cells are cleaned once by a phosphate buffer solution (PBS), and then reacted with a Trypsin-EDTA solution at 37 degrees Celsius for 5 minutes, and then the cell spatula is used to remove incompletely reacted cells carefully, and the same proportion of a medium containing a fetal bovine serum is used for neutralizing the enzyme activity of trypsin. The number of cells is measured by a cell counter (Vi-CELL AS, Beckman Coulter). The survived cell is distinguished from a dead cell by using 0.4% Trypan-blue (GIBCO-Invitrogen). In the calculation, the parameter settings for determining the survival rate of the mesenchymal stem cell include 100 images, Size 10-30 microns, 75% spot brightness, and 5% spot area. Each set of experiment data is measured for three times, and the result is expressed in term of mean± standard deviation.

5.1.1 Experiment Result

Figure 4A:
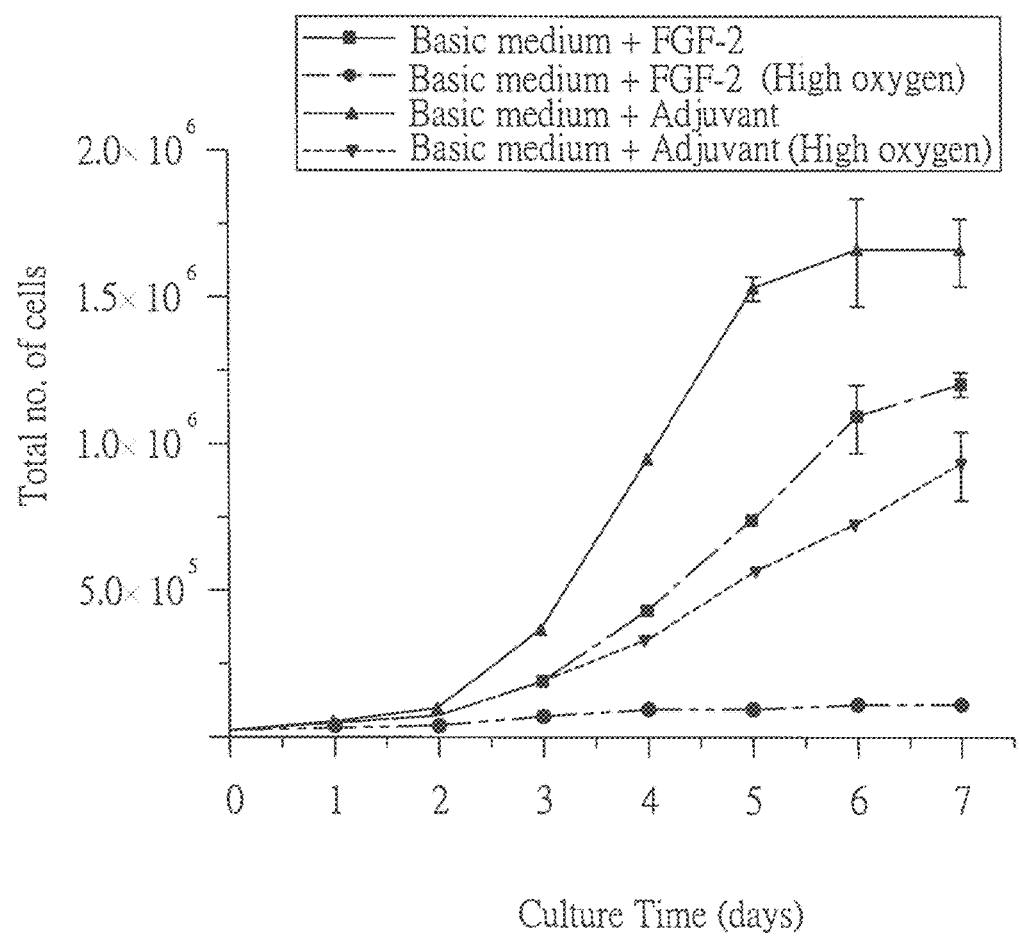
FIG. 4A is a graph of the number of culture days versus the total number of cells after the adipose-derived stem cells are cultured in different conditions in accordance with the present invention.

With reference to FIG. 4A for the graph of the number of culture days versus the total number of cells when the adipose tissue-derived stem cells are cultured at different culture conditions, the result shows that as the number of culture days increases, the number of cells of the culture group with the basic medium and the adjuvant of the present invention in the normal oxygen environment starts increasing rapidly from the second day and reaches a quantity above $1.5 \times 10^6$ on the fifth day, which is obviously greater and faster than the culture group with the basic medium and FGF-2 in the normal oxygen environment. On the other hand, the number of cells of the culture group with the basic medium and FGF-2 in the high oxygen environment increases very slowly, and the total number of cells is still below $2.5 \times 10^6$ on the seventh day, and thus the high oxygen environment is unfavorable for the cell proliferation. In addition, the total number of cells of the culture group with the basic medium and the adjuvant of the present invention in the high oxygen environment tends to increase rapidly from the second day, when compared with the culture group with the basic medium and FGF-2 in the high oxygen environment. On the sixth day, the total number of cells reaches a quantity above $1.0 \times 10^6$, which is obviously greater and faster than the culture group with the basic medium and FGF-2 in the high oxygen environment. Therefore, the culture by adding the adjuvant of the present invention in the normal oxygen environment has a faster cell proliferation rate and produces more cells than the culture group with the basic medium with the adjuvant of the present invention in the high oxygen environment. Although the culture is taken place in the high oxygen environment which is unfavorable for the cell proliferation, the adjuvant of the present invention can reduce the unfavorable effect of the cell proliferation caused by the high oxygen environment, so that some of the cells can be proliferated continuously.

5.2 Effect of Adipose Tissue-Derived Stem Cell Cultured at Different Culture Conditions on the Expression of p21 and CDK2 Proteins The culture conditions of the adipose tissue-derived stem cell are divided into four groups as described in the aforementioned section 5. The Western Blot Analysis is used for the analysis to observe the effect of the controlling and adjusting the cell cycle related proteins of the adipose tissue-derived stem cells cultured in different culture conditions on the protein expression of the cell cycle related proteins (such as p21 and CDK2). Similarly, the expression of the β-actin protein is used as a control for the standardization of quantifying each aforementioned protein expression into data.

5.2.1 Experiment Result

Figure 4B:
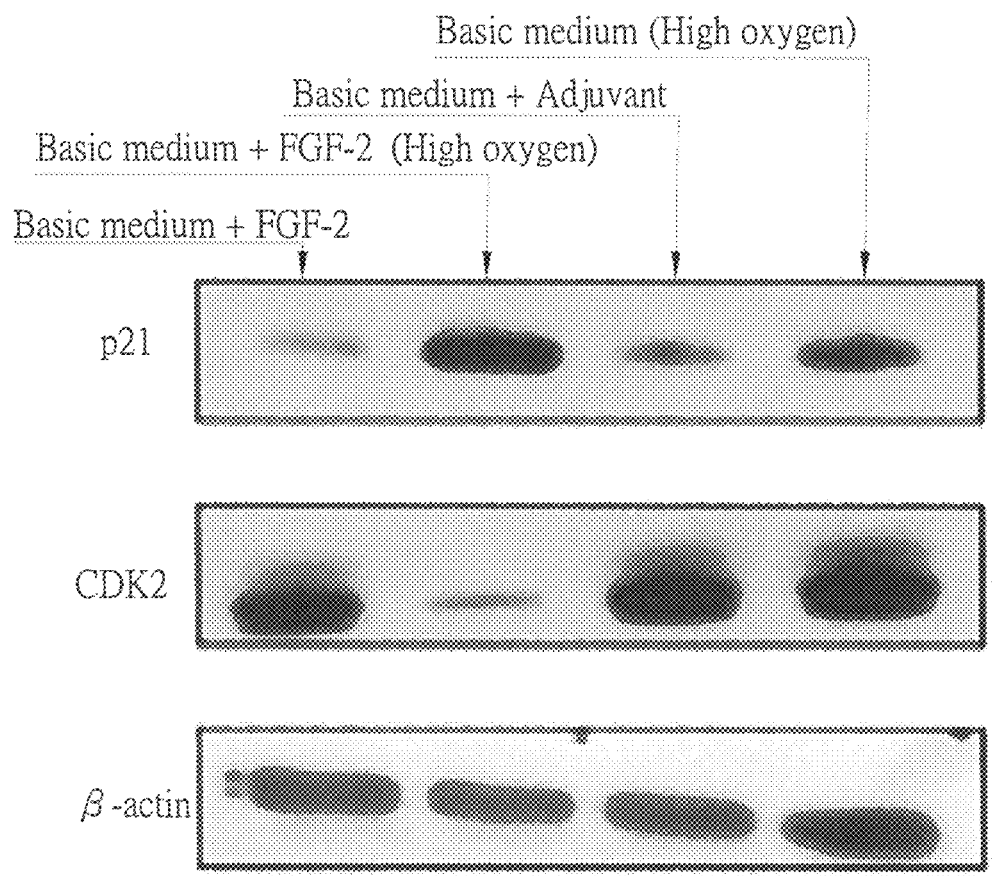
FIG. 4B are photographs showing the effect of adipose-derived stem cells cultured in different conditions in accordance with the present invention on the protein expression responsible for controlling and adjusting the cell cycle.

With reference to FIG. 4B, the result shows that the expression level of the p21 protein of the culture group with the basic medium and FGF-2 in the normal oxygen environment and the culture group with the basic medium and the adjuvant of the present invention in the normal oxygen environment decreases, but the expression level of the CDK2 protein increases. On the other hand, the culture group with the basic medium and FGF-2 in the high oxygen environment has a significant increase of the expression of the p21 protein due to the high oxygen environment, so as to inhibit the expression of the CDK2 protein which is unfavorable to cell proliferation. It is noteworthy that the culture group with the basic medium and the adjuvant of the present invention in the high oxygen environment has an obviously lower expression of the p21 protein than the culture group with the basic medium and FGF-2 in the high oxygen environment. Although the culture is taken place in the high oxygen environment, yet the adjuvant of the present invention is added, so that the expression of the CDK2 protein increases significantly. Once again, it shows that the addition of the adjuvant of the present invention can improve the proliferation rate of the mesenchymal stem cell significantly over the culture without adding the adjuvant of the present invention, regardless of the normal oxygen environment or the high oxygen environment.

Experiment 2: Effect of Adipose Tissue-Derived Stem Cells Cultured in Different Serum Additives in Cell Proliferation The cell culture conditions of this experiment are divided into four groups, respectively: a group with a basic medium and 10% fetal bovine serum, a group with a basic medium and 10% human serum, a group with a basic medium, 10% human serum and the adjuvant of the present invention, and a group with a basic medium, 2% human serum and the adjuvant of the present invention. The basic medium is an Iscove's modified Dulbecco's medium, GIBCO-Invitrogen (IMDM) added with 2 mM-glutamine (BCO-Invitrogen), and the adjuvant of the present invention includes 2 mM N-acetyl-L-cysteine (NAC, Sigma) and 0.2 mM AsA2P (Sigma).

In each group of stem cells, the cells with a cell density of 3000 cells/cm2 are cultured in 6-well plates (Becton Dickinson), and all cells are cultured at in an incubator (Forma Series II Model 3110, Thermo) with the environment of a temperature of 37 degrees Celsius, a partial pressure of carbon dioxide approximately equal to 5% and a humidity of 95%, and the medium is changed once every three days. The culture takes place weekly and the medium is changed once every three days. The effects of different human mesenchymal stem cells at different culture conditions on the cell proliferation are observed for 7 days.

1. Cell Growth Density Analysis

Each group of stem cells is cleaned once by a phosphate buffer solution (PBS), and then reacted with a Trypsin-EDTA solution at 37 degrees Celsius for 5 minutes, and then the cell spatula is used to remove incompletely reacted cells carefully, and the same proportion of a medium containing fetal bovine serum is used for neutralizing the enzyme activity of trypsin. The number of cells is measured by a cell counter (Vi-CELL AS, Beckman Coulter). The survived cell is distinguished from a dead cell by using 0.4% Trypan-blue (GIBCO-Invitrogen). In the calculation, the parameter settings for determining the survival rate of the mesenchymal stem cell include 100 images, Size 10-30 microns, 75% spot brightness, and 5% spot area. Each set of experiment data is measured for three times, and the result is expressed in term of mean±standard deviation.

1.1 Experiment Result

Figure 5A:
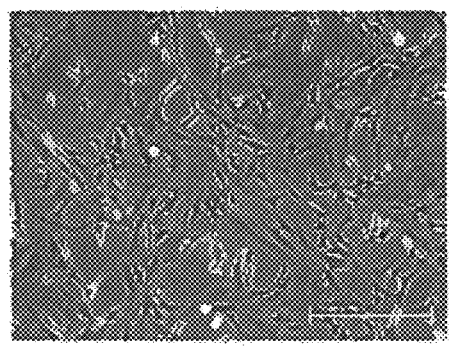
FIG. 5A shows the number and morphology of the cells after the adipose-derived stem cells are cultured in different conditions.
Figure 5A:
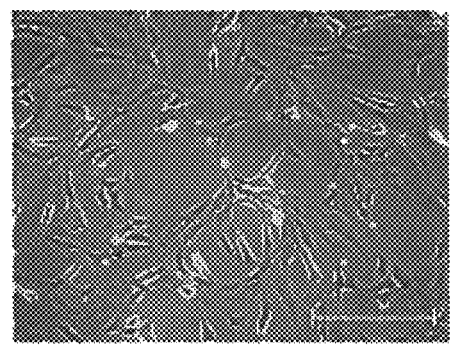
Figure 5A:
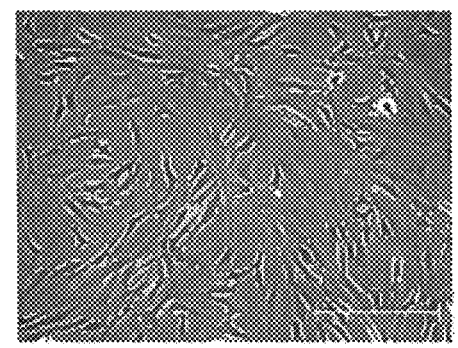
Figure 5A:
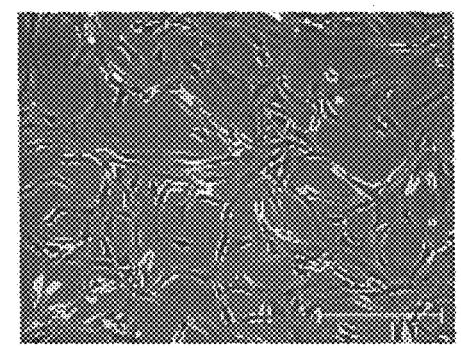
Figure 5B:
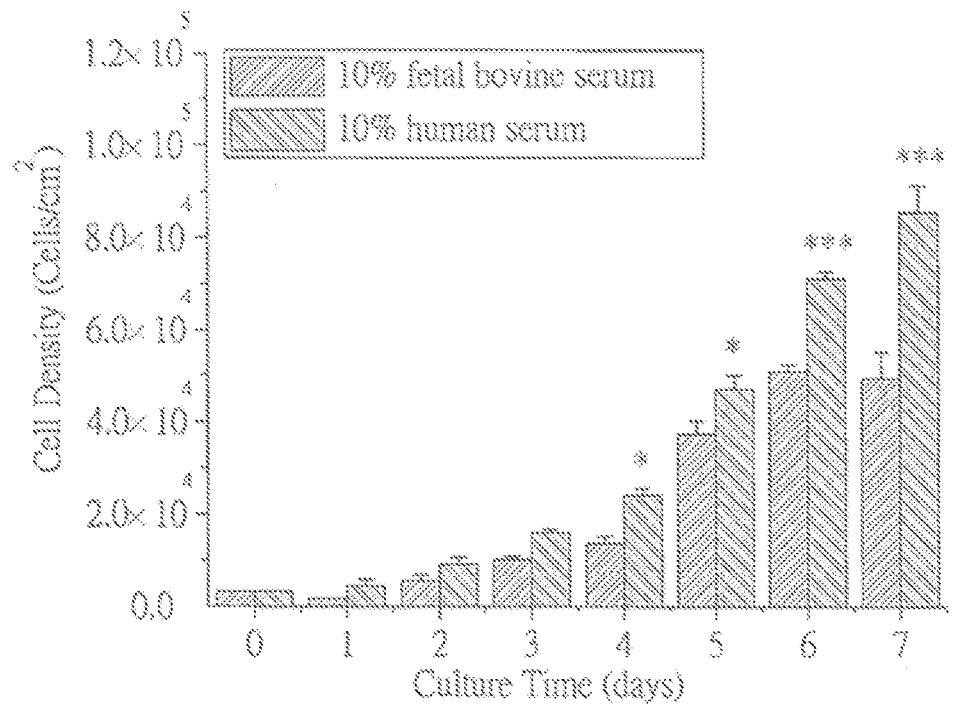
FIGS. 5B, 5C and 5D are a graph the number of cells versus the number of culture days of an adipose-derived stem cell after the adipose-derived stem cells are cultured in different conditions in accordance with the present invention.
Figure 5C:
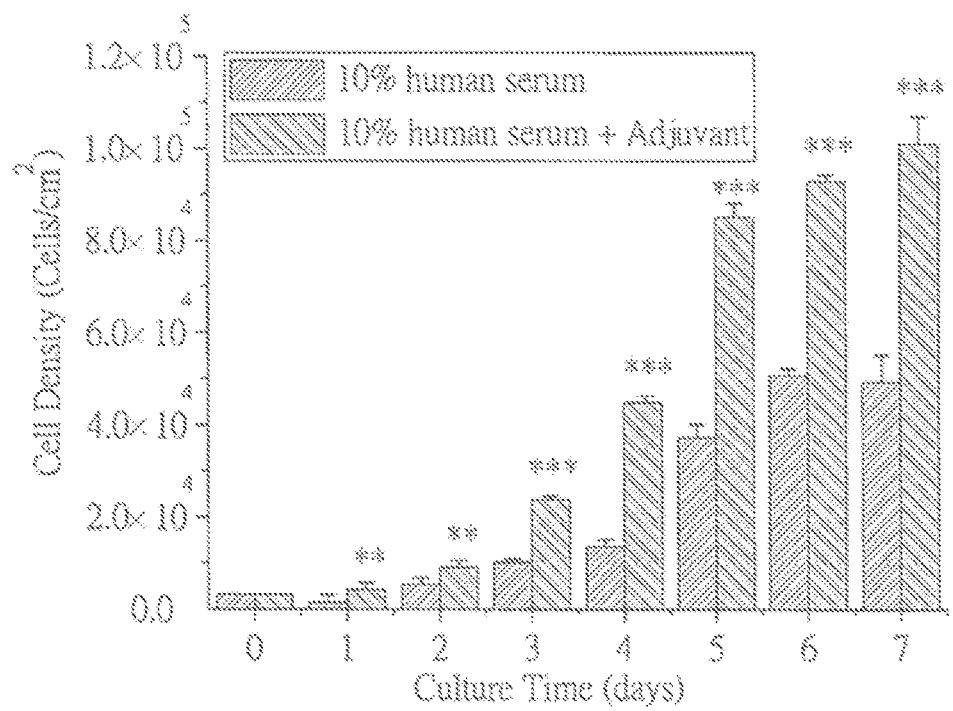
Figure 5D:
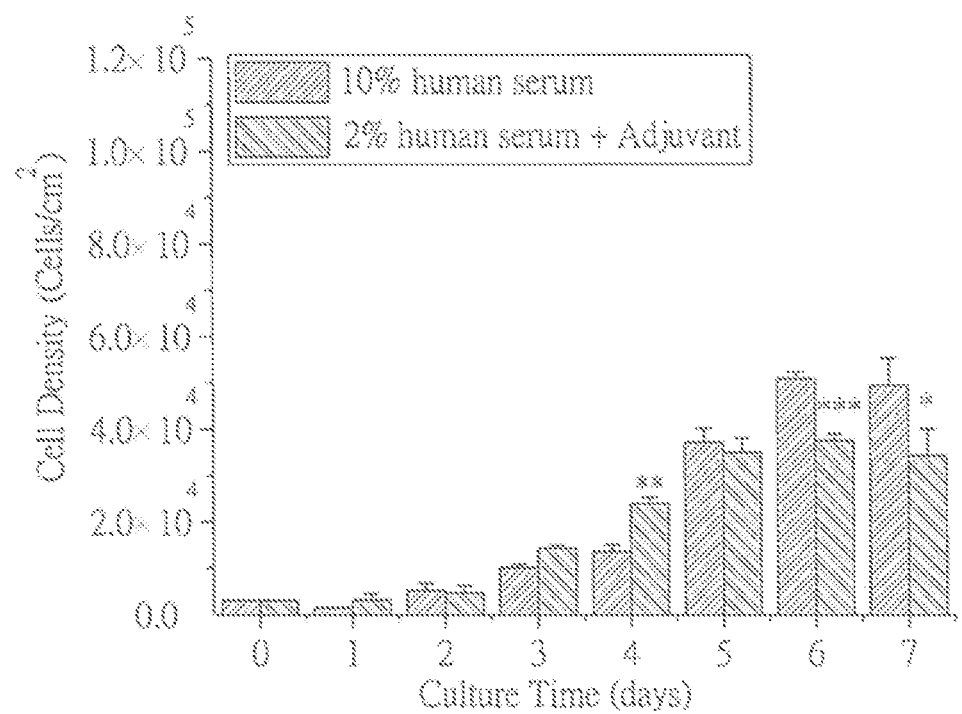

The data of the aforementioned experiment are processed by Microsoft Excel t-test statistical analysis, wherein the level of significance $p<0.05$, the data are quantified in a chart, * $P<0.05$,  $P<0.01$, and * $P<0.005$. With reference to FIG. 5A for the adipose tissue-derived stem cells cultured in different culture conditions and being in a cell morphology observed by a microscope with a scale of 500 microns (μm), the observation shows that the type of each tissue cell is similar and in a form of a fusiform cell. With reference to FIG. 5B for the graph of number of culture days versus cell density of the group with the basic medium and 10% fetal bovine serum and the group with the basic medium and 10% human serum, the cell density of the group with the basic medium and 10% human serum starts improving than the group with the basic medium and 10% fetal bovine serum is increased by approximately 28% to 74% after four days of the culture, and there is a significant difference. Therefore, using the human serum as the serum additive for the cell culture can achieve a faster proliferation of the adipose tissue-derived stem cell than adding the fetal bovine serum. With reference to FIG. 5C for the comparison of cell density of the group with the basic medium and 10% human serum and the group with the basic medium, the 10% human serum, and the adjuvant of the present invention, the result shows that the number of cells of the group with the basic medium, the 10% human serum, and the adjuvant of the present invention has increased by 155% to 324% than the group with the basic medium and the 10% human serum after one day of the culture, and there is a significant difference. Therefore, the culture by adding the adjuvant of the present invention can further increase the cell proliferation rate of the adipose tissue-derived stem cells, so as to obtain a larger number of cells in the same number of culture days. With reference to FIG. 5D for the comparison between the group with the basic medium and 10% human serum and the group with the basic medium, the 2% human serum and the adjuvant of the present invention, the result shows that although the group with the basic medium, 2% human serum and the adjuvant of the present invention only has 2% of human serum, yet the adjuvant of the present invention added for the culture still can achieve the same cell proliferation rate of the adipose tissue-derived stem cells similar to that of the group with the basic medium and 10% human serum in the first 5 days of the culture. Obviously, the addition of the adjuvant of the present invention not only reduces the consumption of human serum, but also maintains the fast proliferation effect of the adipose tissue-derived stem cells.

2. Cell Surface Antigen Analysis of Classic Mesenchymal Stem Cell

The cell surface antigen of the Experiment is measured by a flow cytometry (FACSCalibur, Becton Dickinson). The aforementioned four groups of adipose tissue-derived stem cells cultured in different culture condition are attached and washed by a phosphate buffer solution and then re-dissolved in an appropriate quantity of the phosphate buffer solution, and different antigens are stained by using a corresponding immunofluorescence primary antibody including CD13, CD34, CD44, CD73, CD90, CD105, β2 microglobulin (B2M) and HLA-DR antibodies (Becton Dickinson). The staining process is conducted at room temperature for 15 minutes in a dark place, and after the appropriate quantity of phosphate buffer solution is added, the groups are analyzed and data are collected by the flow cell meter, and finally analyzed by the flow cytometry analysis software (FACSCalibur, Becton Dickinson). Wherein, the negative control group omits the staining process of the primary antibody.

2.1 Experiment Result

Figure 6A:
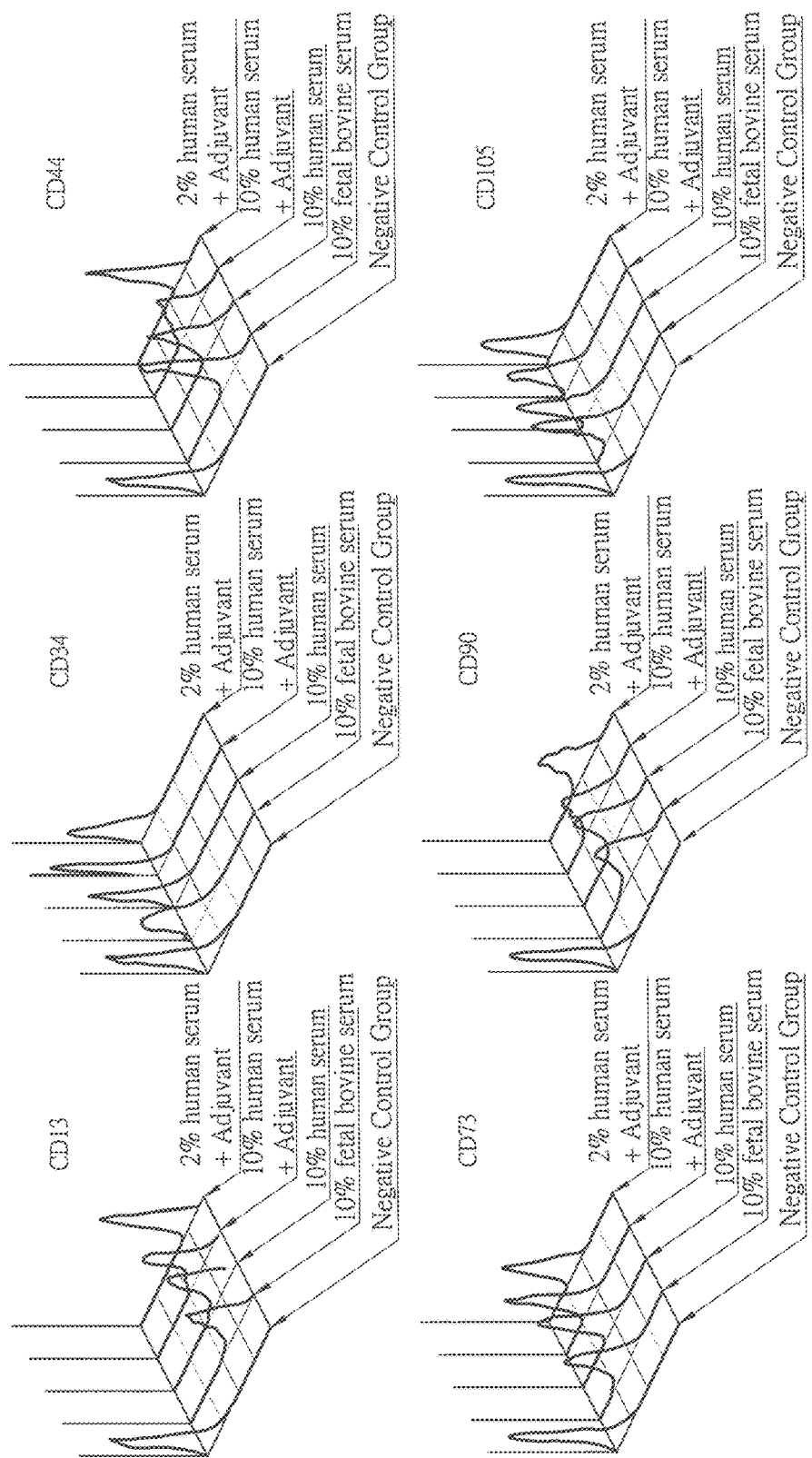
FIG. 6A shows the analyses of an antigent on a cell surface of the adipose-derived stem cell cultured in different conditions in accordance with the present invention.

In FIG. 6A, the result shows that the cell groups of the aforementioned four groups of adipose tissue-derived stem cells cultured in different culture conditions are CD13+, CD34−, CD44+, CD73+, CD90+, and CD105+, which are cell groups similar to the mesenchymal stem cell. In other words, the aforementioned four groups of adipose tissue-derived stem cells cultured in different culture conditions still maintain the characteristics similar to the surface antigen of the mesenchymal stem cell. Wherein, the expression of CD44 and CD73 of the three experiment groups added with the human serum is higher than the group with the basic medium and 10% fetal bovine serum, and this result indicates that the three experiment groups with the added human serum culture maintains the characteristics similar to the surface antigen of the mesenchymal stem cell and achieves a better culture effect than the group with the added fetal bovine serum.

3. Stem Cell Gene Expression Analysis

In this experiment, the gene related expression of undifferentiated stem cells of the adipose tissue-derived stem cells obtained from culturing the aforementioned four groups at different culture conditions are analyzed by a real-time polymerase chain reaction system (Real-Time PCR System). After the cultured cells are washed by a phosphate buffer solution and collected in a 1.5-ml eppendorf, and 1 ml of TriZol (10296-010, Invitrogen) reagent is added, and the mixture is placed at room temperature for 5 minutes, and 100 μl of BCP (BP. 151, MRC) solution is added and mixed by Vortex to produce a pink solution, and then the solution is placed at room temperature for 15 minutes, and centrifuged at 4° C. at 15,000 g for 15 minutes.

After the centrifuge is completed, the interior of the eppendorf is divided into three layers, wherein the bottom layer is a red layer, the middle layer is a thin white layer, and the top layer is a transparent layer. The top layer is removed by suction and placed into a new 1.5-mL eppendorf, and the suction process must be performed carefully to avoid sucking the other two layers. In the new eppendorf, 0.5 mL of isopropanol is added and shaken uniformly, and then placed at room temperature for 30 minutes, and then centrifuged at 4° C. at 15,000 g for 10 minutes to extract a supernatant without sucking the pellet, and 1 mL of 75% ethanol is added for washing, and then centrifuged at 4° C. at 15,000 g for 10 minutes. After the ethanol is extracted, an air dry process takes place for 10 minutes, and a re-dissolution takes place by using water for inhibiting the RNase (DEPC), so as to complete the RNA extraction. Approximately 10 μg of RNA is sucked, and a reverse transcription reagent kit (RT-for-PCR kit, Clontech) is added. After a polymerase chain reaction machine (PCR machine) is used to complete the reverse transcription, a polymerase (GoTaq Green Master Mix, M7122, Promega) is added to perform the polymerase chain reaction, the settings for the reaction can be adjusted slightly according to a different Tm value of a different primer. The analysis is related to the genes of undifferentiated stem cell such as Nanog, SOX2, CXCR4, TERT, etc. The primers used in each gene for the analysis of this experiment, Nanog, SOX2, CXCR4, TERT and the β-actin gene of the control group are listed in the following table.

| Gene | Primer Sequence (5' to 3') | Product Size (bp) |
|---|---|---|
| β-actin | Forward: CGCCAACCGCGAGAAGAT<br>Reverse: CGTCACCGGAGTCCATCA | 168 |
| Nanog | Forward: AATACCTCAGCCTCCAGCAGAT<br>Reverse: TGCGTCACACCATTGCTATTCTT | 148 |
| SOX2 | Forward: AGACCAGTACCCGCATCT<br>Reverse: CGCTCCGCCTCCTCCAC | 108 |
| CXCR4 | Forward: CGTGGAACGTTTTTCCTGTT<br>Reverse: TGTAGGTGCTGAAATCAACCC | 129 |
| TERT | Forward: GGTTTTTGAGGGTGAGGGTGAGGGTGAGGGTGAGGGT<br>Reverse: TCCCGACTATCCCTATCCCTATCCCTATCCCTA | >76 |

3.1 Experiment Result

Figure 6B:
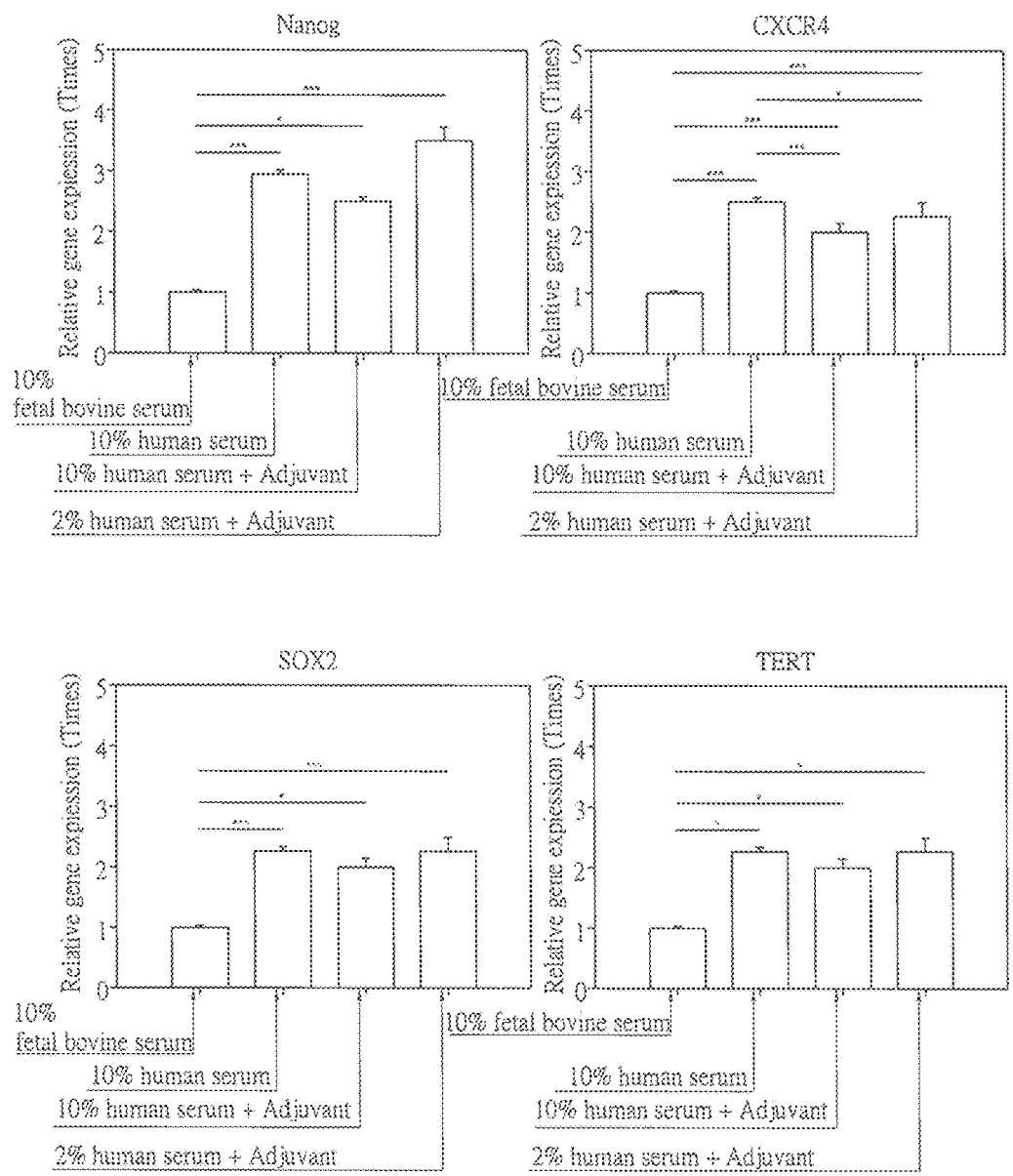
FIG. 6B shows the analyses of relative expression of genes after the adipose-derived stem cells are cultured in different conditions in accordance with the present invention.

With reference to FIG. 6B, the result shows that the expression of the genes related to the undifferentiated stem cell (Nanog, SOX2, CXCR4, TERT) of the three experiment groups with added human serum (10% human serum, 10% human serum+adjuvant, 2% human serum+adjuvant) is obviously higher than the group with the basic medium and 10% fetal bovine serum group, and we also observed that although the group with the basic medium, 2% human serum, and the adjuvant of the present invention only has 2% of human serum, yet after the adjuvant of the present invention is added for the culture, the expression of the aforementioned stem cell genes can be maintained to a level as the culture added with 10% human serum. Therefore, the adjuvant of the present invention used in the cell culture can surely reduce the consumption of the human serum.

4. Differentiation of Adipose Tissue-Derived Stem Cells

Related journals reported that the adipose tissue-derived stem cell is capable of differentiating mesoderm cells such as adipocytes and osteogenic cells. Similar to Experiment 2, this experiment also divides into four groups and cultures the adipose tissue-derived stem cells at different culture conditions for six days, and then the stem cells are induced and differentiated into osteogenic cells, chondrocytes and adipocytes to confirm whether or not the aforementioned four groups cultured at different culture conditions for six days still have the multifunctional differentiation ability of the stem cells. In the induction and differentiation experiment of the present invention, a conventional stem cell induction and differentiation system (Kanda et al., 2011; Song et al., 2010) is adopted, but this is not the key point of the invention, and thus will not be described, and whose main purpose is to confirm whether or not the aforementioned four groups cultured at different culture conditions of the present invention still have the multifunctional differentiation ability of the stem cells.

4.1 Chemical Staining and Molecular Marker Analysis of Cells

The differentiated osteogenic cell is stained by an alkaline phosphatase (Alkaline phosphatase, ALP), and the alkaline phosphatase is an important index of the differentiation of mature osteoblast, and the staining method is a conventional staining technique (Yoshimura et al., 2011), and thus will not be described. In addition, a conventional Von-kossa staining method is used to confirm the existence of calcium phosphate. For the differentiated chondrocyte, the Alcian blue staining method is used to confirm the existence of proteoglycan in the cartilage tissue (Song et al., 2010). For the differentiated adipocyte, an Oil red O staining is used to confirm whether or not a lipid vacuole exists (Kanda et al., 2011). In addition, this experiment aims at the expression of a molecular marker [a gene such as Core-Binding Factor 1 (cbfa1), an Osteocalcin (OC) and a type I collagen (COL IA1)] of the osteogenic cell, and the expression of a molecular marker [a gene such as cartilage glycoprotein (ACAN), a type II collagen (COL IIA1)] of the chondrocyte, and the lipid synthesis related genes of the adipocyte [Peroxisome proliferator-activated receptor γ(PPARγ) and adipocyte fatty-acid binding protein (aP2)], and the β-actin gene is used as a control group to perform a real-time polymerase chain reaction and analyze the corresponding expression level. The primer used in each gene is listed below:

| Gene | Primer Sequence (5' to 3') | Product Size (bp) |
|---|---|---|
| β-actin | Forward: CGCCAACCGCGAGAAGAT<br>Reverse: CGTCACCGGAGTCCATCA | 168 |
| Cbfa1 | Forward: TGGCAGCACGCTATTAAATC<br>Reverse: TCTGCCGCTAGAATTCAAAA | 103 |
| OC | Forward: CAAAGTCTAACTAGGGATACC<br>Reverse: AGAGATGAGTCTGTCCTG | 150 |
| COL IA1 | Forward: GACTCTAAGATCAGAGACGGAGAC<br>Reverse: TCGCTGACATCTCCATTCATTCAC | 250 |
| ACAN | Forward: TACACTGGCGAGCACTGTAAC<br>Reverse: CAGTGGCCCTGGTACTTGTT | 71 |
| COL IIA1 | Forward: GAATAGCACCATTGTGTAGGAC<br>Reverse: AATGCCCCCTGAGTGAC | 97 |
| PPARγ | Forward: TTGCTGTCATTATTCTCAGTGGA<br>Reverse: GAGGACTCAGGGTGGTTCAG | 124 |
| aP2 | Forward: GACATCAGCGCCTACATCG<br>Reverse: GGCTGTGCTGGAACAGGT | 70 |

4.2 Experiment Result

Figures 7A, 7B:
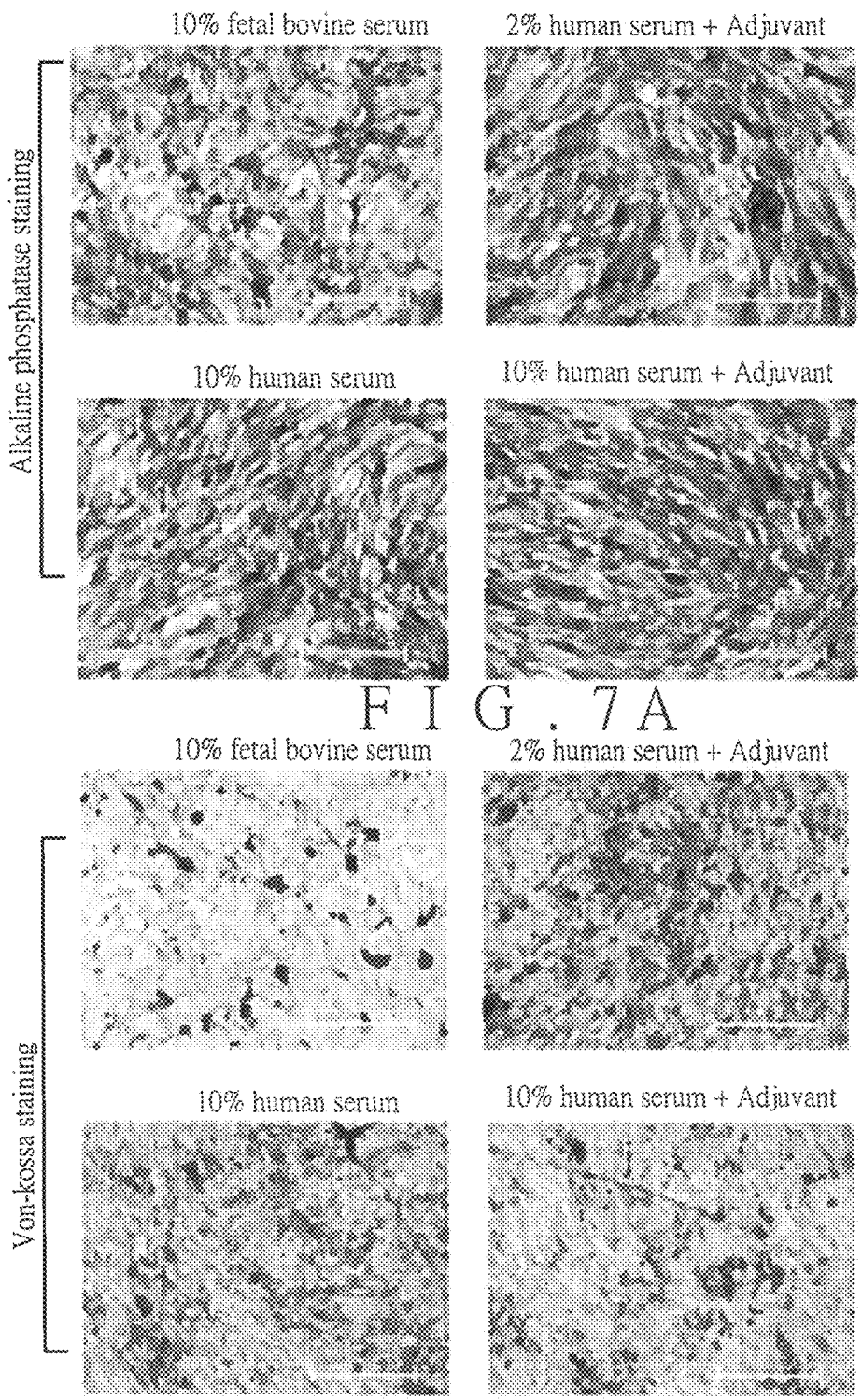
FIGS. 7A and 7B are photographs showing that the adipose-derived stem cells are cultured in different conditions in accordance with the present invention and inductively differentiated into osteogenic cells and processed by a chemical staining process.
Figure 7C:
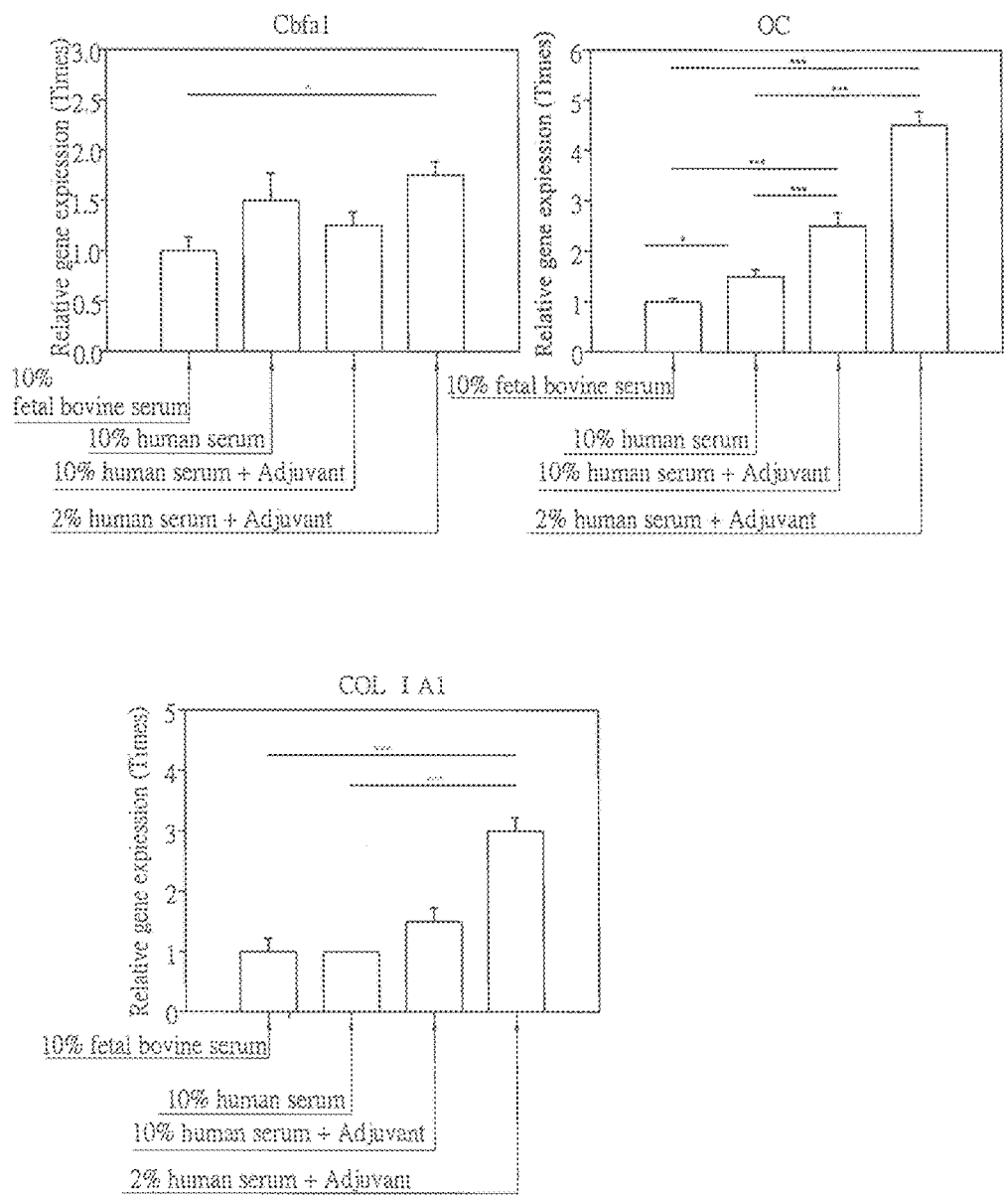
FIG. 7C shows the relative expression analysis of molecular markers of osteogenic cell after the adipose-derived stem cells cultured in different conditions in accordance with the present invention and induced and differentiated into an osteogenic cell.

With reference to FIG. 7A for the alkaline phosphatase staining result, the scale is 500 microns (μm), and the adipose tissue-derived stem cells of the aforementioned four groups are cultured at different culture conditions and induced and differentiated into osteogenic cells. After the alkaline phosphatase staining process, a portion of black crystals appears, thus indicating the existence of the alkaline phosphatase and showing that all of the four groups can maintain the stem cell differentiation ability of the adipose tissue-derived stem cells. With reference to FIG. 7B for the Von-kossa staining result, the scale is 500 microns (μm), all of the aforementioned four groups have black or dark brown calcium phosphate crystals. Once again, it shows that the four groups can maintain the stem cell differentiation ability of the adipose tissue-derived stem cells. With reference to FIG. 7C for the molecular marker expression analysis result of the osteogenic cell, it is found that in the relative expression level of the osteocalcin (OC), the group with the basic medium, 10% human serum and the adjuvant of the present invention and the group with the basic medium, 2% human serum and the adjuvant of the present invention have a molecular marker expression of the osteogenic cell higher than that of the group with the basic medium, 10% fetal bovine serum, and the group with the basic medium and 10%, wherein * P<0.05,  P<0.01, and * P<0.005. In particular, the group with the basic medium, 2% human serum and the adjuvant of the present invention has relative expression levels of the cbfa1, OC and COL IA1 higher than that of the group with the basic medium and 10% fetal bovine serum group. The adjuvant of the present invention added into a human serum for culturing the adipose tissue-derived stem cells can maintain the original differentiation ability of the stem cells, and the effect is even better if the stem cells are induced and differentiated into osteogenic cells.

Figure 8A:
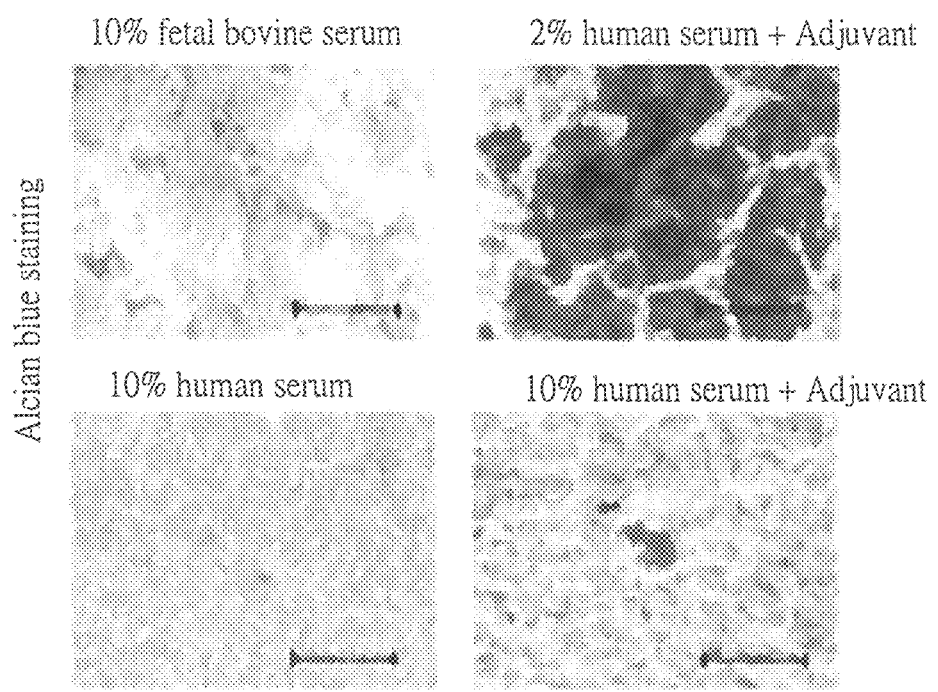
FIG. 8A shows the chemical staining results of adipose-derived stem cells cultured in different conditions in accordance with the present invention and induced and differentiated into a chondrocyte.
Figure 8B:
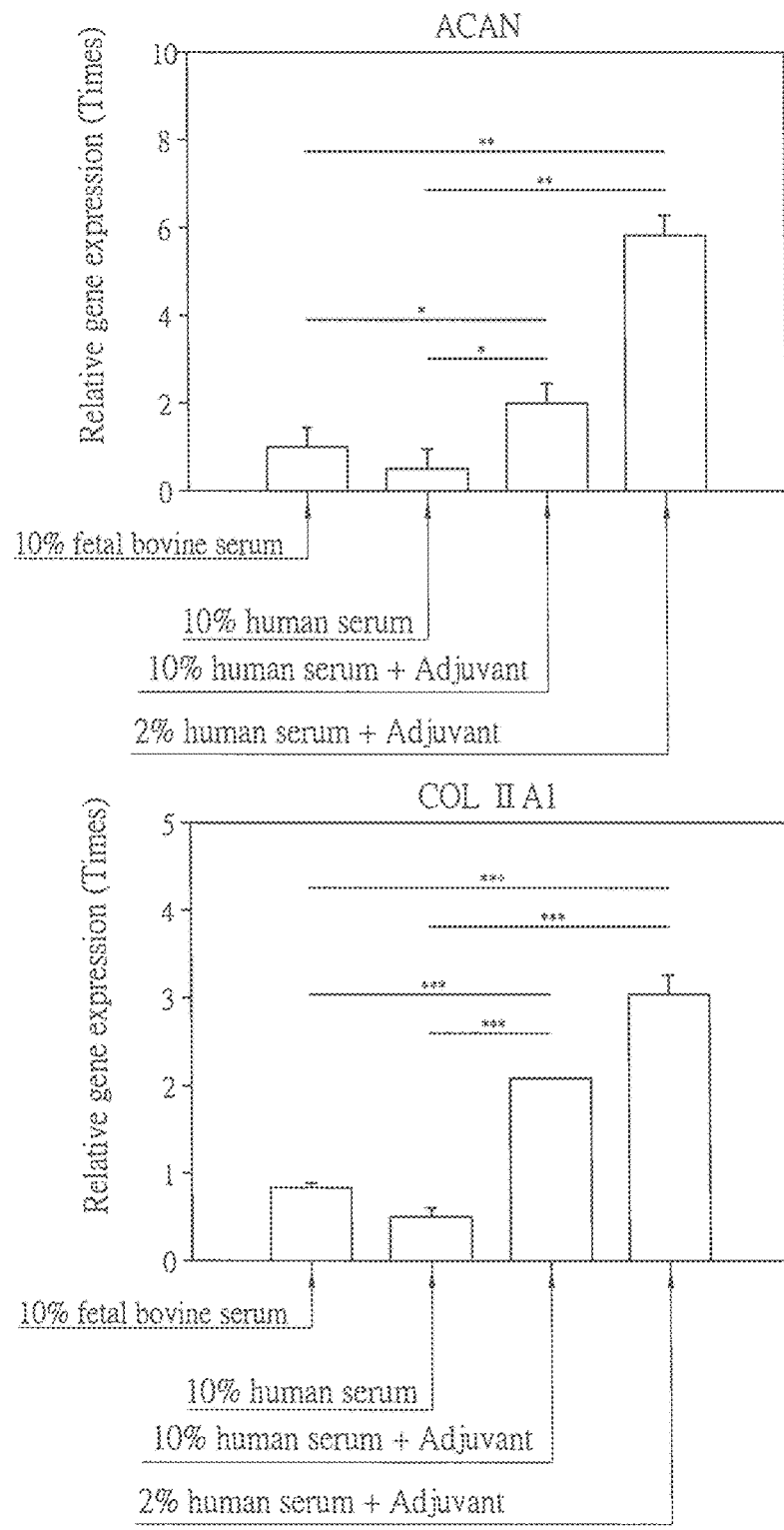
FIG. 8B shows the relative expression analysis of molecular markers of chondrocytes after the adipose-derived stem cells cultured in different conditions in accordance with the present invention and induced and differentiated into a chondrocyte.
Figure 8C:
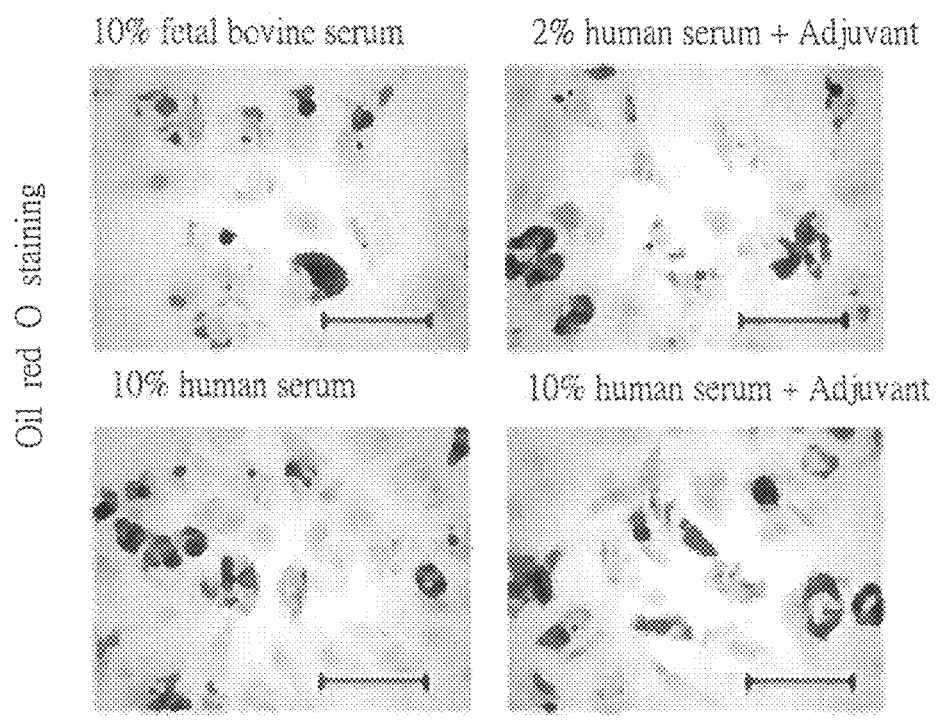
FIG. 8C shows the chemical staining results of adipose-derived stem cells cultured in different conditions in accordance with the present invention and induced and differentiated into an adipocyte.
Figure 8D:
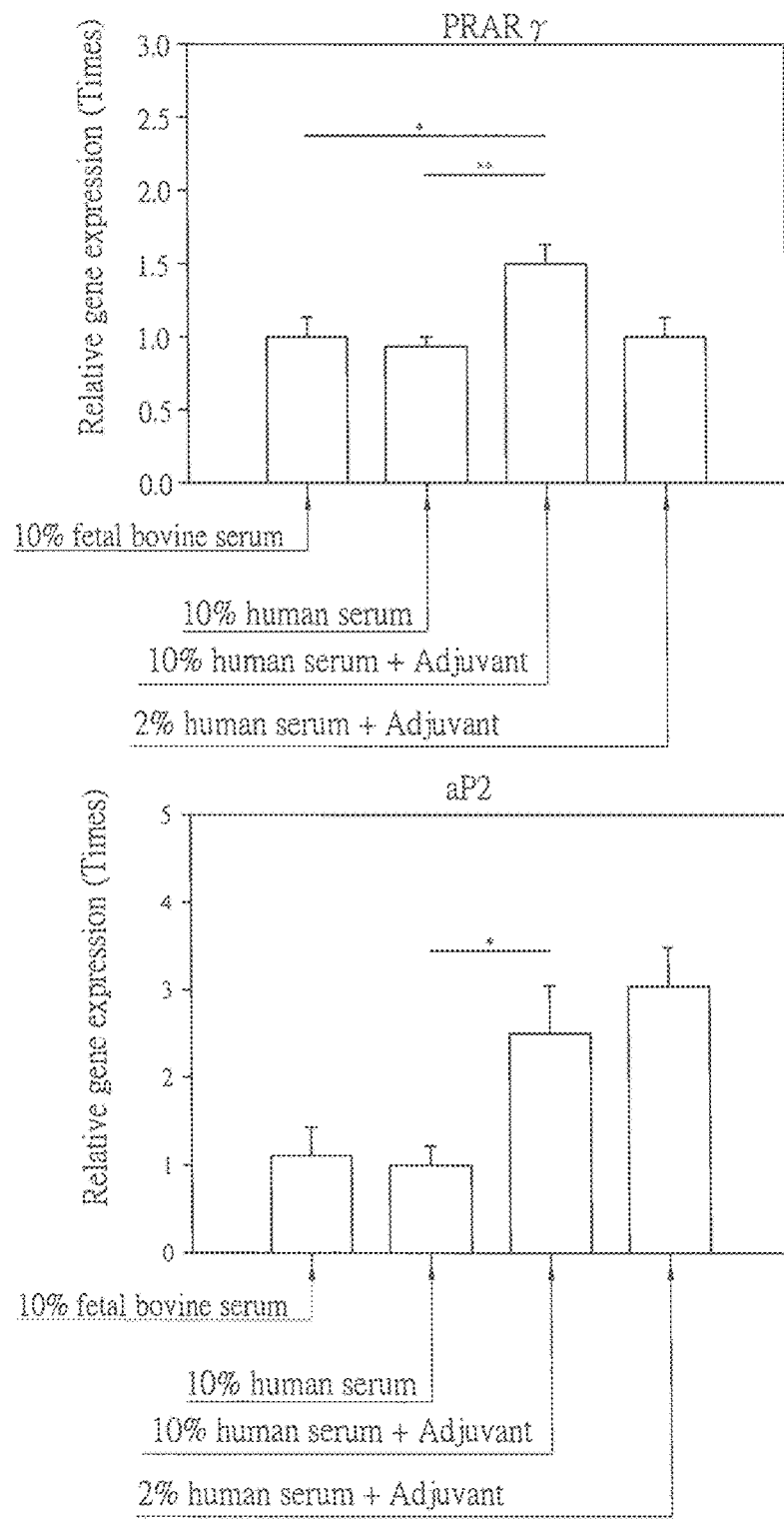
FIG. 8D shows the relative expression analysis of molecular markers of adipocytes after the adipocyte after the adipose-derived stem cells cultured in different conditions in accordance with the present invention and induced and differentiated into an adipocyte.

With reference to FIG. 8A for the Alcian blue staining result, the scale is 500 microns (μm), and it is found that the aforementioned four groups has blue proteoglycan staining, particularly the group with the basic medium, 2% human serum, and the adjuvant of the present invention has a blue proteoglycan staining are much greater than the other three groups. With reference to FIG. 8B for the molecular marker expression analysis of the chondrocyte, it is found that the group with the basic medium, 10% human serum and the adjuvant of the present invention and the group with the basic medium, 2% human serum and the adjuvant of the present invention have a relative expression level of the gene such as ACAN and COL IIA1 significantly higher than that of the group with the basic medium and 10% fetal bovine serum and the group with the basic medium and 10% human serum, wherein * P<0.05,  P<0.01, and * P<0.005. In particular, the group with the basic medium, 2% human serum and the adjuvant of the present invention has a much higher molecular marker expression of the chondrocyte. Therefore, the culture of adipose tissue-derived stem cells by adding the adjuvant the present invention to human serum can maintain the original differentiation ability of the stem cells and the stem cells induced and differentiated into chondrocyte have a better effect. With reference to FIG. 8C for the oil red O staining result, the scale is 500 microns (μm), and it is found that all of the aforementioned four groups have a red lipid vacuole staining result. With reference to FIG. 8D for the relative expression levels of lipid synthesis related gene PPARγ and aP2, * P<0.05, and ** P<0.01. It is found that the group with the basic medium, 10% human serum, and the adjuvant of the present invention has a relative expression level of PPARγ and aP2 higher than the group with the basic medium and 10% fetal bovine serum and the group with the basic medium and 10% human serum.

Therefore, the culture of adipose tissue-derived stem cells by adding the adjuvant the present invention to human serum can maintain the original differentiation ability of the stem cells and the stem cells induced and differentiated into adipocyte have a better effect.

5. Cytokine Array Analysis and Relative Gene Expression Analysis

This experiment performs the analysis by using the adipose tissue-derived stem cells in three different statuses (10% human serum before the culture, and 10% human serum for the culture and 10% human serum with the adjuvant culture) by taking the supernatant of the medium which is available in the market and includes 41 kinds of human cytokine array analysis kits (Cat #AAH-GF-1, Ray-Biotech, Norcross, Ga.). The effect of the adipose tissue-derived stem cells of the aforementioned three statuses on the secreted cytokine and growth factor is analyzed. The analysis method of the aforementioned array analysis kit is not the key point of the invention, and thus will not be described, and refer to RayBiotech's catalog (Cat #AAH-GF-1) for details. Similar to the analysis method as described in Section 3 of Experiment 2, this experiment also aims at the genes including specific growth factors such as insulin-like growth factor (IGF-1), hepatocyte growth factor (HGF) and epidermal growth factor (EGF) and uses β-actin gene as a control group for the four groups of adipose tissue-derived stem cells cultured at different culture conditions to perform the real-time polymerase chain reaction (Real-Time PCR) to analyze the relative expression level. The primers used for analyzing each gene are listed in the following table.

| Gene | Primer Sequence (5' to 3') | Product Size (bp) |
|---|---|---|
| β-actin | Forward: CGCCAACCGCGAGAAGAT<br>Reverse: CGTCACCGGAGTCCATCA | 168 |
| IGF-1 | Forward: AAGATGCACACCATGTCC<br>Reverse: TGTTGAAATAAAAGCCCCTG | 157 |
| HGF | Forward: TGTTCCCTTTTTTGGGTAAGC<br>Reverse: CCCATTTGCCACAGAAAGTT | 148 |
| EGF | Forward: CTAATCACCTACTCAATGCCTGG<br>Reverse: TGATTCTCCCAGTACTCTTACTTGG | 109 |

In addition, this experiment also aims at the following three culture conditions of the adipose tissue-derived stem cell, including the culture of a group with a basic medium and 10% fetal bovine serum, a group with a basic medium and 10% fetal bovine serum (in a low oxygen environment of 5% partial pressure of oxygen) and a group with a basic medium, 10% fetal bovine serum, and the adjuvant of the present invention, and the supernatant of the medium is used to perform a human cytokine array analysis (Cat #AAH-GF-1, RayBiotech, Norcross, Ga.) to observe the effect of the adipose tissue-derived stem cells on the secretion of cytokine and growth factor.

5.1 Experiment Result

Figure 9A:
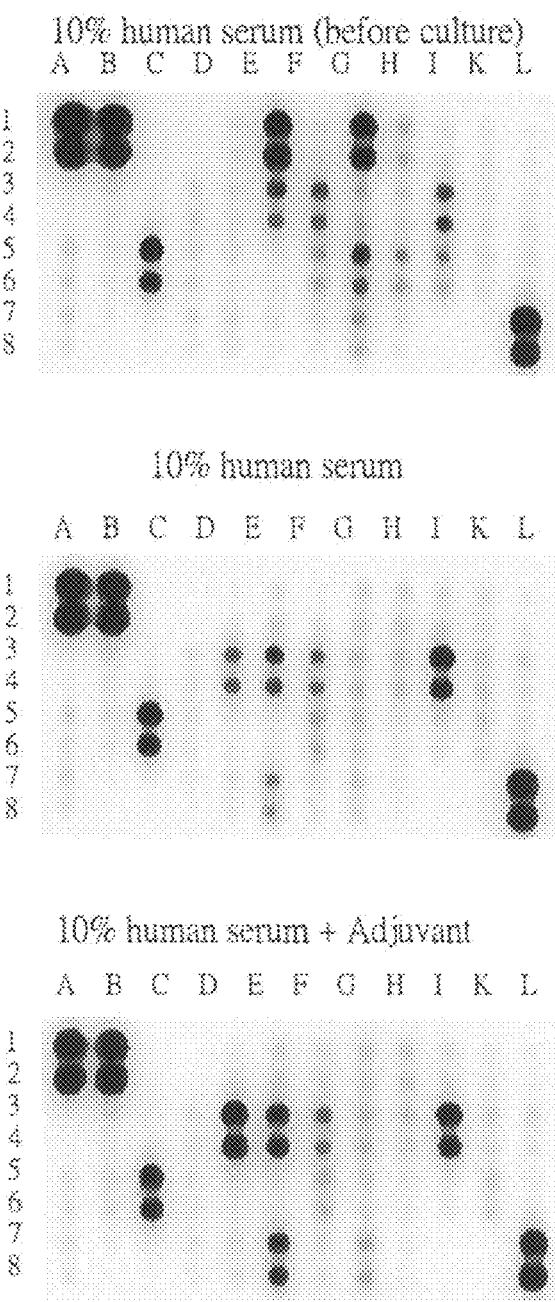
FIG. 9A are photographs showing the cytokine array analysis of the adipose-derived stem cells cultured in different conditions in accordance with the present invention.
Figure 9C:
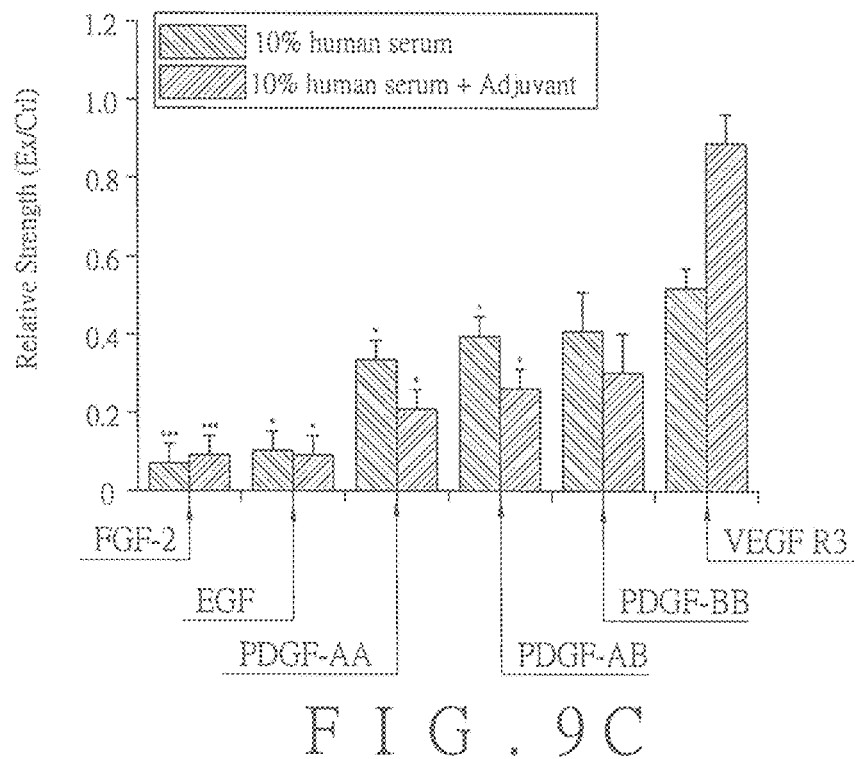
FIGS. 9C and 9D are charts of the relative expression quantitative analysis of the cytokine as depicted in FIG. 9B.
Figure 9D:
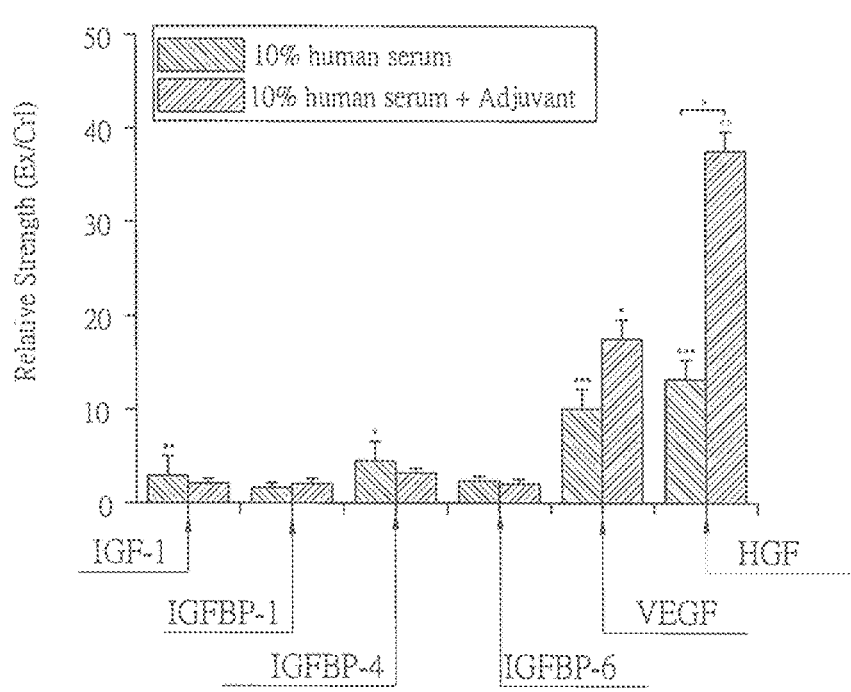

With reference to FIGS. 9A and 9B for the cytokine array analysis result and the comparison of the cytokine array analysis result, POS represents a positive control group, NEG represents a negative control group, * $P<0.05$,  $P<0.01$, and * $P<0.005$. The result shows that after the adjuvant culture of the present invention is added into the adipose tissue-derived stem cells, the conditional medium secretes the following cytokines and growth factors: FGF-2, EGF, FGF-4, FGF-6, FGF-7, HB-EGF, HGF, IGFBP-1, IGFBP-2, IGFBP-3, IGFPB-4, IGFBP-6, IGF-I, IGF-I SR, IGF-II, M-CSF, M-CSF R, PDGF Rα, PDGF-Rβ, PDAF-AA, PDGF-AB, PDGF-BB, PIGF, SCF, TGF-β3, VEGF, and VEGF R2. In FIG. 9B, the culture of 10% human serum before the culture and the culture of 10% human serum are compared, and the blocks arranged diagonally towards the lower left corner are a basic fibroblast growth factor (bFGF), an epidermal growth factor (EGF), a blood platelet derivative growth factor (PDGF-AA, AB, BB) and a vascular endothelial growth factor (VEGF R3), which are absorbed by the cells, and the blocks arranged diagonally towards the lower right corner are a hepatocyte growth factor (HGF), an insulin-like growth factor binding protein (IGFBP-1, IGFBP-4, IGFBP-6), an insulin-like growth factor 1 (IGF-1), and a vascular endothelial growth factor (VEGF) which is secreted from the cell into the medium. With reference to FIGS. 9C and 9D for the comparison of the culture results of the aforementioned 10% human serum culture and 10% human serum with the adjuvant, it is found that the blood platelet derivative growth factor (PDGF-AA, AB, BB) keeps being absorbed and used by the cells, and the hepatocyte growth factor (HGF), insulin-like growth factor binding protein (IGFBP-1) and vascular endothelial growth factor (VEGF) are secreted from the cells into the medium, and the culture result by adding 10% human serum and the adjuvant is improved significantly. Therefore, the culture of the adipose tissue-derived stem cell by adding the adjuvant of the present invention and the human serum can improve the secretion of certain growth factors such as HGF, IGFBP-1 and VEGF.

Figure 9E:
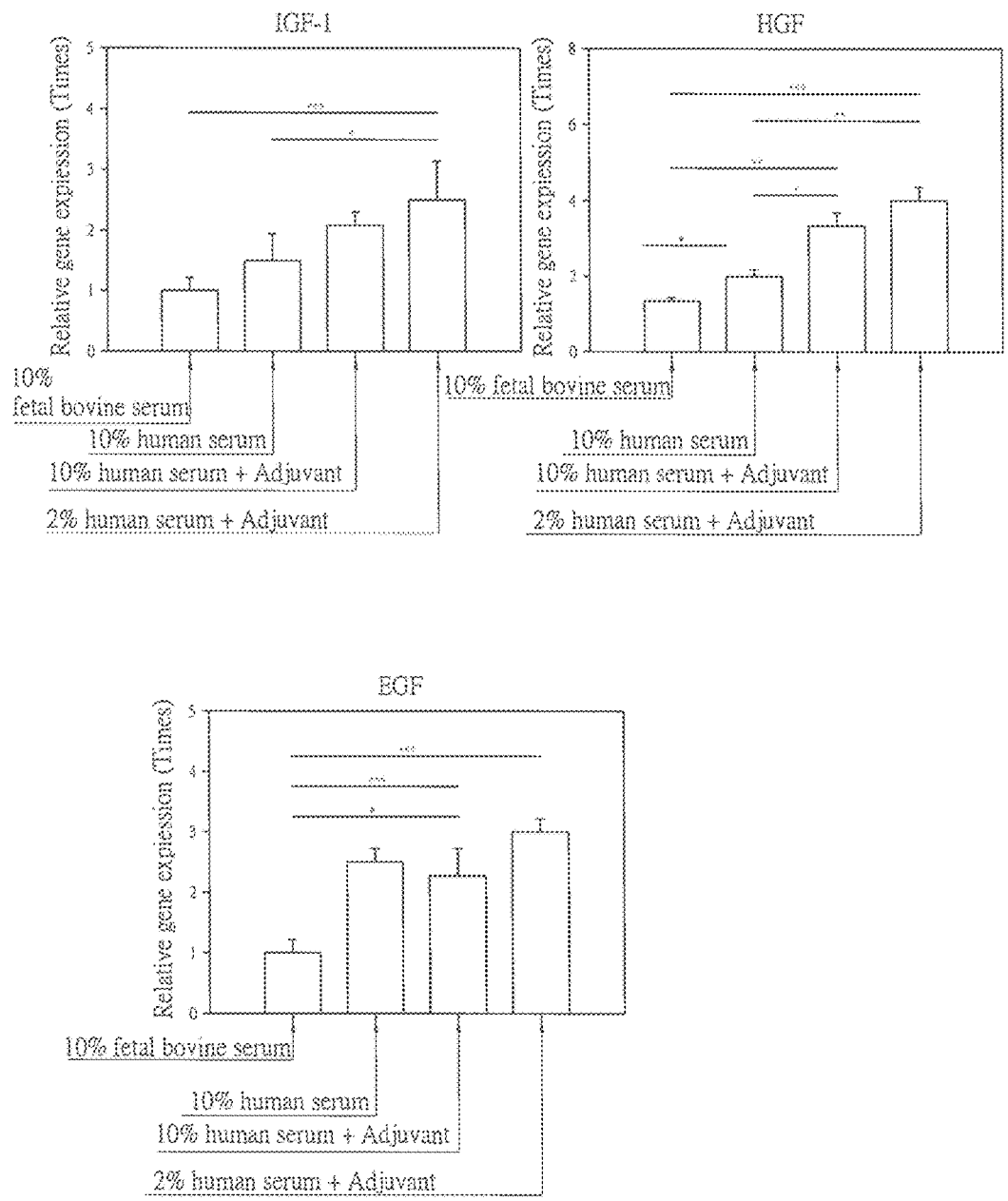
FIG. 9E are charts showing the relative expression analysis of the cytokine after the adipose-derived stem cells are cultured in different conditions in accordance with the present invention.

With reference to FIG. 9E for the relative expression levels of the growth factors IGF-1, HGF and EGF of the four groups of adipose tissue-derived stem cells cultured in different culture conditions, * $P<0.05$,  $P<0.01$, and * $P<0.005$. The result shows that in the culture of the three groups with added human serum (10% human serum, 10% human serum+adjuvant, 2% human serum+adjuvant), the relative expression levels of the IGF-1, HGF and EGF are higher than the group with the basic medium and 10% fetal bovine serum, particularly the relative expression level of the group with the basic medium, 2% human serum and the adjuvant of the present invention is the highest. Therefore, the culture of the adipose tissue-derived stem cells by adding the adjuvant of the present invention to the human serum can improve the relative expression level of the growth factor such as IGF-1, HGF and EGF.

Figure 9F:
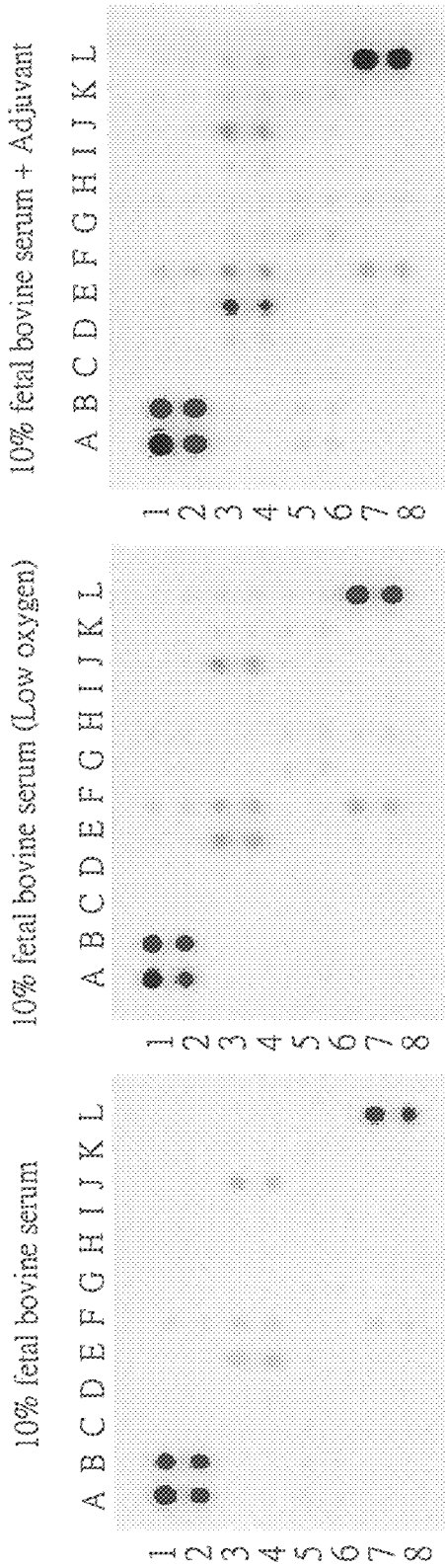
FIG. 9F shows the cytokine array analysis after the adipose-derived stem cells are cultured in different conditions in accordance with the present invention.

With reference to FIGS. 9F and 9G for the comparison between the cytokine array analysis result and the aforementioned cytokine array analysis result, an empty dot in the block of each cell factor in FIG. 9G represents the group of adipose tissue-derived stem cells with the basic medium and 10% fetal bovine serum group having this cytokine. Similarly, a solid dot represents a group of adipose tissue-derived stem cells with the basic medium and 10% fetal bovine serum (in a low oxygen environment of 5% partial pressure of oxygen) has this cytokine, and the shaded dot represents a group of adipose tissue-derived stem cells with the basic medium, 10% fetal bovine serum and the adjuvant of the present invention that secretes the cytokine or growth factor. In FIG. 9G, the cytokine or growth factor such as bFGF, EGF, HB-EGF, HGF, IGFBP-1, IGFBP-2, IGFBP-6, IGF-II, M-CSF, M-CSF R, NT-4, PDGF Rβ, PIGF, TGF-β3, VEGF, etc is secreted in the culture condition of the adipose tissue-derived stem cells secretes. It is noteworthy that although the group with the basic medium and 10% fetal bovine serum (in a low oxygen environment of 5% partial pressure of oxygen, and a group with the basic medium, 10% fetal bovine serum and the adjuvant of the present invention) can increase the kinds of cytokine secreted from the adipose tissue-derived stem cells, but the group with the basic medium, 10% fetal bovine serum and the adjuvant of the present invention can increase the kind and quantity even more (such as the following cytokine or growth factor: β-NGF, FGF-4, FGF-6, FGF-7, IGFBP-3, IGFBP-4, IGF-I, IGF-I SR, GCSF, GDNF, GM-CSF, PDGF-AA, PDGF-AB, PDGF-BB, SCF, VEGF R2, VEGF R3, and VEGF-D. Therefore, the culture of adipose tissue-derived stem cell by adding the adjuvant of the present invention in different culture conditions can increase the kind and quantity of cytokines or growth factors secreted from the adipose tissue-derived stem cells than those of the culture taken place in a low oxygen environment culture.

In summation of the aforementioned results, the adipose tissue-derived stem cell containing a basic medium of 10% fetal bovine serum regardless of the culture by adding the adjuvant of the present invention and the human serum or simply adding the adjuvant of the present invention can achieve the fast proliferation effect, while harvesting a large quantity of secreted growth factors during the culture of the adipose tissue-derived stem cells, wherein the culture with the adjuvant of the present invention and the basic medium of the human serum has the best culture condition, so that the stem cells can be used in a wound healing medicine, the manufacture of a wound healing medicine, a skin care product, and the manufacture of a skin care product.

Experiment 3: The Microcarrier Culture of Adipose Tissue-Derived Stem Cell

Most of the human mesenchymal stem cells cultured in vitro adopt the anchorage-dependent cell culture method, so that an attaching type culture system is used for producing a large quantity of quality cells to be used in the fields of regenerative medicine and tissue engineering. This experiment uses a spinner microcarrier culture flask (Spinner Flasks, Bellco Glass, Inc., Vineland, N.J., USA) for the culture of the adipose tissue-derived stem cells. Before the cells are inoculated into the flask, the internal surface of the culture flask is processed with silicone (Sigmacote, Sigma, St. Louis, Mo., USA), and the microcarriers (CultiSpher-G; HyClone, Logan, Utah, USA) are weighed according to the procedure as described in the User Manual, and water is added and mixed, and a sterilizer is used for the processing for 15 minutes 121° C. Before the cells are mixed, extra phosphate buffer solution is removed, and then a desired culture liquid for culturing the cells is added for a balance for approximately 24 hours. The adipose tissue-derived stem cells are added into a mixing culture reactor containing a total of 50 mL of the pre-balanced culture liquid and the microcarrier. At the beginning, an external electromagnetic mixing system is turned on intermittently, and a break of 10 to 20 minutes is taken after two hours of operation at the frequency of 25 r.p.m for 30 minutes. After the aforementioned two hours, the culture starts at a rotation speed of 25 r.p.m, and the culture liquid is changed once every 3 days, and 50% to 70% of the culture liquid is changed each time. The mixing process is stopped for approximately 5 minutes before changing the culture liquid, so that the cells and the microcarriers can fall to the bottom of the reactor. Wherein, the microcarrier culture process taken place in the environment of 37° C., humidity 95% and 5% partial pressure of carbon dioxide for the culture for 7 days, and the medium contains IMDM added with 10% human serum, 2 mM L-glutamine, and the adjuvant of the present invention; and the adjuvant contains 10 ng/mL FGF-2, 2 mM N-acetyl-L-cysteine (NAC), and 0.2 mM L-scorbic acid-2-phosphate (AsA2P).

To observe the growth and distribution of the cells on the microcarrier, 1 mL of cell fluid containing the microcarrier is taken daily, and the medium is removed by centrifuge and washed once by a phosphate buffer solution, and then after 10% formalin fixative solution is used for the fixation at room temperature for 10 minutes, the fixative solution is washed away by a phosphate buffer solution, and then 5 mg/mL green fluorescent sodium diacetate (FDA) and 2 mg/mL propidium iodide (PI) are used for staining the live cells and dead cells. After the stained cells are placed in a dark place at room temperature for 5 minutes, the dye is removed and a phosphate buffer solution is used for washing for three times, and then the cells and the microcarrier are placed and distributed uniformly on a glass slide, and observation is made by using the fluorescence microscope.

Experiment Result

Figure 10B:
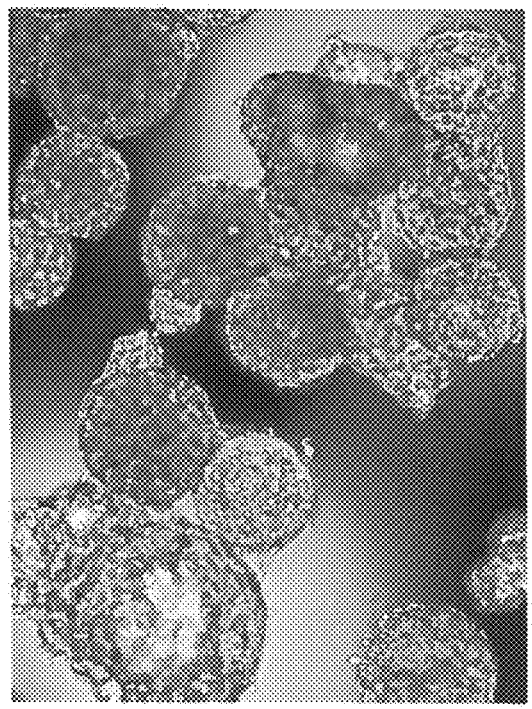
FIG. 10B shows the fluorescent photographs of FIG. 10 of the present invention.
Figure 10A:
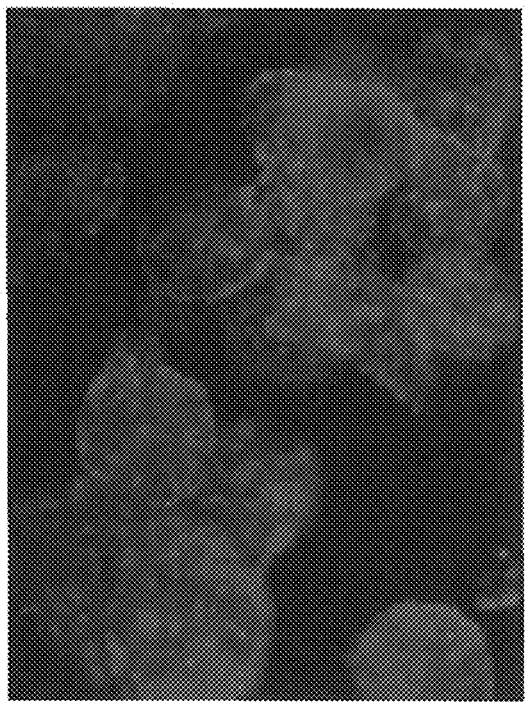
FIG. 10A shows the optical microscopic photographs of micro-carriers of the cultured adipose tissue-derived stem cells in accordance with the present invention.

With reference to FIGS. 10A and 10B, the adipose tissue-derived stem cell is cultured in a microcarrier for seven days, and images are observed from an optical microscope and a fluorescence microscope, wherein green fluorescence represents live cell and red fluorescence represents dead cell. From the images in FIG. 10B, the adipose tissue-derived stem cell can be attached onto the microcarrier more easily to define a microstructure status. Therefore, the adipose tissue-derived stem cell cultured in a biocompatible material such as the microcarrier can form a microstructure status which can be used in the following regenerative medicine or tissue engineering.

In summation of the aforementioned experiment result, the adjuvant for rapid proliferation of human mesenchymal stem cells in vitro in accordance with the present invention is added into a medium containing human mesenchymal stem cells, and after the culture is taken place in a normal oxygen environment (with a partial pressure of oxygen approximately equal to 21%), a rapid cell division occurs similar to the culture taken place in a low oxygen environment (with a partial pressure of oxygen approximately equal to 5%), and the proportion of the cell cycle S phase is increased, so as to reduce the ageing and improving the differentiation potential. In addition, when the fetal bovine serum is substituted by the human serum for the culture, a better cell proliferation rate is achieved, and the quantity and kind of growth factors secreted by the cells are increased. Therefore, the present invention not only amplifies the human mesenchymal stem cells rapidly and effectively, but also maintains the multifunctional characteristic of the stem cells, and achieves the effects of amplifying the human mesenchymal stem cells rapidly and harvesting the growth factor effectively.

While the invention has been described by means of specific embodiments, numerous modifications and variations could be made thereto by those skilled in the art without departing from the scope and spirit of the invention set forth in the claims.

What is claimed is:

1. A method for promoting proliferation of human mesenchymal stem cells in vitro, comprising the step of adding an adjuvant comprising an antioxidant and a basic fibroblast growth factor (FGF-2), wherein the antioxidant comprises 0.2-0.6 mM long-acting ascorbic acid phosphate derivative and 1.0-2.5 mM N-acetyl-L-cysteine (NAC), into a medium containing the human mesenchymal stem cells and 2% human serum.

2. The method for promoting proliferation of human mesenchymal stem cells in vitro according to claim 1, wherein the human mesenchymal stem cell is one selected from the group consisting of an adipose tissue-derived stem cell, a bone marrow mesenchymal stem cell and an umbilical cord mesenchymal stem cell.

3. The method for promoting proliferation of human mesenchymal stem cells in vitro according to claim 1, wherein the long-acting ascorbic acid phosphate derivative is an L-ascorbic acid-2-phosphate (AsA2P).

4. The method for promoting proliferation of human mesenchymal stem cells in vitro according to claim 1, wherein the basic fibroblast growth factor (FGF-2) has a concentration from 1 to 20 nanograms per milliliter.

5. The method for promoting proliferation of human mesenchymal stem cells in vitro according to claim 1, wherein the adjuvant improves the expression of a cyclin-dependent kinase-2 (CDK-2), a cyclin-dependent kinase-4 (CDK-4) and a cell division cycle protein (CDC2) by inhibiting the expression of cyclin-dependent kinase inhibitors which are p21 and p27 proteins of the human mesenchymal stem cells.

6. The method for promoting proliferation of human mesenchymal stem cells in vitro according to claim 1, further comprising a step of cryopreserving the human mesenchymal stem cells for further use.

7. A method of creating a cell bank, comprising the steps of promoting proliferation of human mesenchymal stem cells in vitro according to claim 1 and cryopreserving the human mesenchymal stem cells to create the cell bank.

8. The method for promoting proliferation of human mesenchymal stem cells in vitro according to claim 1, further comprising an extraction step for obtaining a cell extract of a human mesenchymal stem cell.

9. The method for promoting proliferation of human mesenchymal stem cells in vitro according to claim 1, further comprising an inductive differentiation step to obtain a cell differentiated from the human mesenchymal stem cells.

10. The method for promoting proliferation of human mesenchymal stem cells in vitro according to claim 9, wherein the cell differentiated from the human mesenchymal stem cells is a cell selected from the group consisting of a osteogenic cell, an adipocyte and a chondrocyte.

11. The method according to claim 1, further comprising the step of obtaining a growth factor from the medium after the human mesenchymal stem cells are cultured.

12. The method according to claim 11, wherein the growth factor includes FGF-2, EGF, FGF-4, FGF-6, FGF-7, HB-EGF, HGF, IGFBP-1, IGFBP-2, IGFBP-3, IGFPB-4, IGFBP-6, IGF-I, IGF-I SR, IGF-II, M-CSF, M-CSF R, PDGF Rα, PDGF-Rβ, PDAF-AA, PDGF-AB, PDGF-BB, PIGF, SCF, TGF-β3, VEGF, or VEGF R2.

13. The method according to claim 11, further comprising a step of preparing a medicine comprising the growth factor for healing a wound or serving as a skin care product, wherein the growth factor is at least one selected from the group consisting of FGF-2, EGF, FGF-4, FGF-6, FGF-7, HB-EGF, HGF, IGFBP-1, IGFBP-2, IGFBP-3, IGFPB-4, IGFBP-6, IGF-I, IGF-I SR, IGF-II, M-CSF, M-CSF R, PDGF Rα, PDGF-Rβ, PDAF-AA, PDGF-AB, PDGF-BB, PIGF, SCF, TGF-β3, VEGF, or VEGF R2.

* * * * *